United States Patent
Kilby et al.

(10) Patent No.: US 11,648,423 B2
(45) Date of Patent: *May 16, 2023

(54) RADIATION BASED TREATMENT BEAM POSITION CALIBRATION AND VERIFICATION

(71) Applicant: Accuray Incorporated, Sunnyvale, CA (US)

(72) Inventors: Warren Kilby, Sunnyvale, CA (US); Petr Jordan, Redwood City, CA (US); John Noll, Sunnyvale, CA (US); Calvin Maurer, Jr., San Jose, CA (US)

(73) Assignee: Accuray Incorporated, Sunnyvale, CA (US)

(*) Notice: Subject to any disclaimer, the term of this patent is extended or adjusted under 35 U.S.C. 154(b) by 0 days.

This patent is subject to a terminal disclaimer.

(21) Appl. No.: 16/797,795

(22) Filed: Feb. 21, 2020

(65) Prior Publication Data

US 2020/0188694 A1 Jun. 18, 2020

Related U.S. Application Data

(63) Continuation of application No. 15/607,217, filed on May 26, 2017, now Pat. No. 10,569,105.

(51) Int. Cl.
*A61B 6/00* (2006.01)
*A61N 5/10* (2006.01)

(52) U.S. Cl.
CPC ............ *A61N 5/1075* (2013.01); *A61B 6/583* (2013.01); *A61N 5/1043* (2013.01); *A61N 5/1065* (2013.01); *A61N 5/1083* (2013.01); *A61N 2005/1076* (2013.01); *A61N 2005/1091* (2013.01)

(58) Field of Classification Search
CPC .. A61N 5/1075; A61N 5/1043; A61N 5/1065; A61N 2005/1076
See application file for complete search history.

(56) References Cited

U.S. PATENT DOCUMENTS

| | | |
|---|---|---|
| 2012/0159043 A1 | 6/2012 | Yeh |
| 2013/0033700 A1 | 2/2013 | Hallil |
| 2015/0085993 A1 | 3/2015 | Scheib |
| 2015/0360056 A1* | 12/2015 | Xing .................... A61N 5/1075 600/1 |

(Continued)

FOREIGN PATENT DOCUMENTS

| | | |
|---|---|---|
| EP | 2939708 A1 | 11/2015 |
| WO | 2012159043 A2 | 11/2012 |

OTHER PUBLICATIONS

Roussakis, Y., Zhang, R., Heyes, G., Webster, G., Mason, S., Green, S., . . . & Dehghani, H. (2015). Real-time Cherenkov emission portal imaging during CyberKnife® radiotherapy. Physics in medicine and biology, 60(22), N419-N425. 7 pages.

(Continued)

*Primary Examiner* — Christine S. Kim
(74) *Attorney, Agent, or Firm* — Womble Bond Dickinson (US) LLP

(57) ABSTRACT

A phantom, calibration system and calibration method are described. The phantom having a phantom body and an X-ray luminescent material, wherein at least a portion of the X-ray luminescent material is on a surface of the phantom.

10 Claims, 18 Drawing Sheets

(56) References Cited

U.S. PATENT DOCUMENTS

| | | |
|---|---|---|
| 2016/0023019 A1 | 1/2016 | Filiberti et al. |
| 2016/0331336 A1 | 11/2016 | Hertz et al. |
| 2017/0219498 A1 | 8/2017 | Chtcheprov et al. |
| 2017/0318652 A1 | 11/2017 | Meiler et al. |

OTHER PUBLICATIONS

Jenkins, C. H., Naczynski, D. J., Shu-Jung, S. Y., Yang, Y., & Xing, L. (2016). Automating quality assurance of digital inear accelerators using a radioluminescent phosphor coated phantom and optical imaging. Physics in medicine and Biology, 61(17), L-29-L37. 10 pages.

Jenkins, C. H., Naczynski, D. J., Shu-Jung, S. Y., Yang, Y., & Xing, L. (2015). Automating quality assurance of digital inear accelerators using radioluminescent phosphor coated phantom and optical imaging. [ PowerPoint slides] Retrieved from AAPM 57th Annual Meeting and Exhibition, Jul. 12-16, 2015. 1 page.

Wang, L., Xing L., Nelson B., (2015). A Novel End-to-End Test System in Assessing the Beam-by-Beam Delivery Accuray for the CyberKnife® System. [PowerPoint slides] 28 pages.

Int'l Search Report and Written Opinion of the ISA/EP in PCT/US2018/033907 dated Jul. 26, 2018; 10 pgs.

\* cited by examiner

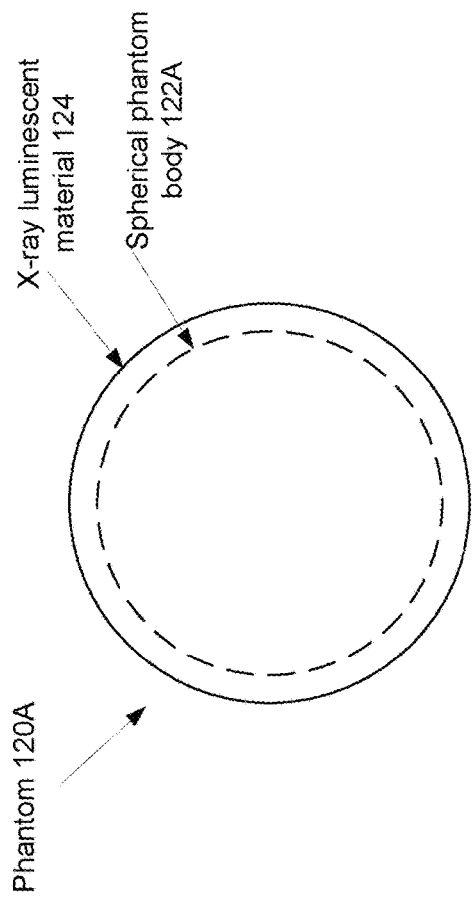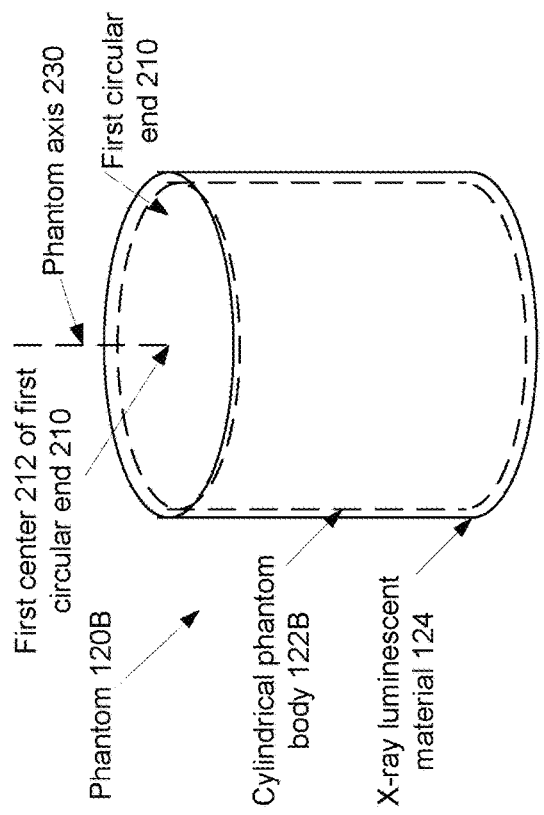

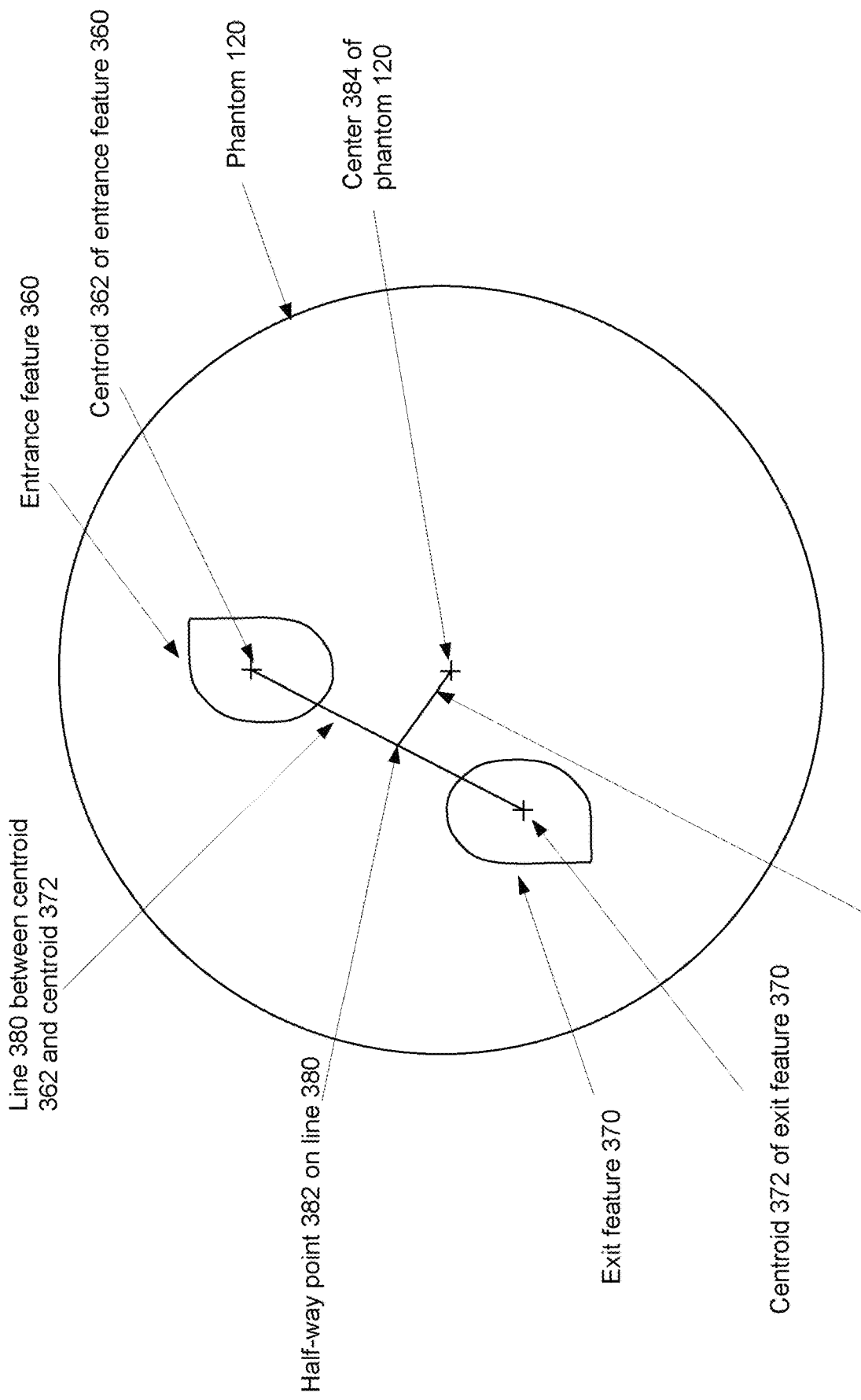

RADIATION BASED TREATMENT BEAM POSITION CALIBRATION AND VERIFICATION

CROSS-REFERENCE TO RELATED APPLICATIONS

This application is a continuation of U.S. application Ser. No. 15/607,217, filed on May 26, 2017, the contents of which are incorporated in its entirety into this application.

TECHNICAL FIELD

Implementations of the present disclosure relate to radiation based treatment beam positions and, in particular, to calibration and verification of radiation based treatment beam positions.

BACKGROUND

A radiation source (e.g., linear accelerator (LINAC)) is used in radiation treatment to apply a beam of highly energized particles (e.g., a radiation beam) to a target within a patient. A mechanical positioning system positions the radiation source (e.g., LINAC) so that the radiation beam is emitted at specific angles and distances (e.g., nodes) relative to the target. Geometric beam delivery accuracy can be improved by performing calibration and verification of the mechanical positioning system.

Calibration techniques may use both a point detector and a raster scan. In a first calibration technique, a surrogate is used for the radiation treatment beam. A point detector (e.g., photodiode) or radiation sensor (e.g., stereotactic diode detector or point scintillation detector) is placed at an isocenter of the mechanical positioning system, a surrogate (e.g., a laser beam) for the radiation beam is emitted, a raster scan of a laser beam (e.g., from a central axis laser) is performed across the point detector or radiation sensor (e.g., an initial coarse scan at 0.8 millimeter (mm) resolution over a larger region and a subsequent finer 0.4 mm resolution scan over a smaller region), and the center of the radiation beam is defined from a resulting maximum optical signal intensity of the surrogate. Axis offsets (used to position the center of the radiation beam in the correct location) are determined and stored as pointing offsets to be applied during radiation treatment.

For a point detector, such a calibration and verification method using a laser as a surrogate may take 100-200 minutes for a node-set containing 100-200 nodes and 17-33 hours for a node-set for a dynamic path involving 1000 nodes. For a radiation sensor, such a calibration and verification method takes even longer. In the above described calibration and verification method, the laser beam acts as a surrogate for the center of the radiation beam, which introduces the uncertainty of coincidence of the laser beam and treatment beam (e.g., laser-to-radiation beam coincidence) in the calibration and verification results. Further uncertainty is added by any variation in instantaneous laser intensity when the maximum optical signal intensity (e.g., peak signal) is used (e.g., laser intensity stability). Uncertainties may also be introduced into the calibration and verification due to sensitivity varying with beam angle of incidence caused by anisotropic construction of the radiation sensor (e.g., detector sensitivity variation with beam orientation).

In a second calibration technique, the radiation treatment beam is used directly. A point detector or radiation sensor is placed at an isocenter of the mechanical positioning system, a radiation beam is emitted using the LINAC, a raster scan is performed across the point detector or radiation sensor, and the center of the radiation beam is defined from a resulting maximum optical signal intensity. Axis offsets are determined and stored as pointing offsets to be applied during radiation treatment. For the second calibration technique, there are not uncertainties from a laser-to-radiation beam coincidence, but the uncertainties caused by dose-rate stability and detector sensitivity variation with beam orientation may cause the time required for calibration and verification under the second calibration technique to be greater than the time required under the first calibration technique.

BRIEF DESCRIPTION OF THE DRAWINGS

The present disclosure is illustrated by way of example, and not by way of limitation, in the figures of the accompanying drawings.

FIG. 2A illustrates a phantom including a spherical phantom body that includes an X-ray luminescent material, in accordance with implementations of the present disclosure.

FIG. 2B illustrates a phantom including a cylindrical phantom body that includes an X-ray luminescent material, in accordance with implementations of the present disclosure.

FIG. 3D illustrates radiation luminescence generated at an entrance surface and an exit surface of the phantom, in accordance with implementations of the present disclosure.

DETAILED DESCRIPTION

Figure 1:
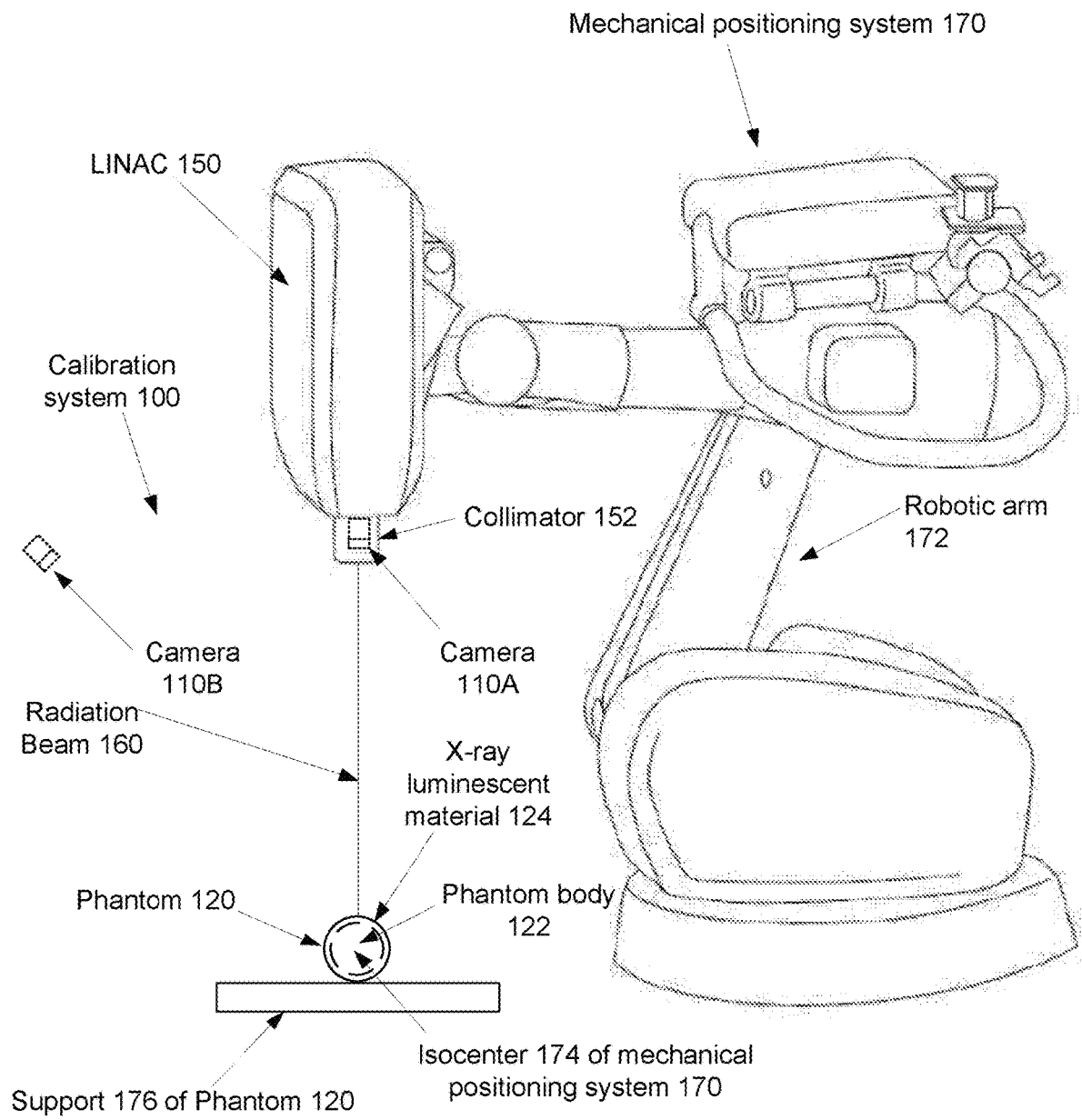
FIG. 1 illustrates a calibration system including one or more cameras and a phantom to calibrate a position of a LINAC, in accordance with implementations of the present disclosure.

A radiation source (e.g., LINAC) is used in radiation treatment to apply a radiation beam to a target within a patient. Implementations of the disclosure often reference LINAC for simplicity and brevity, however, the teaching of the present disclosure are applied to radiation sources generally and can be applied to various types of radiation sources, including for example, LINAC, radioactive isotopes (e.g., cobalt-60), cyclotron, etc. A radiation treatment plan is established by determining pointing vectors for each trajectory of the radiation beam (e.g., via in-room imaging of the target) and then determining positions of the LINAC (e.g., nodes, angle and distance relative to the target) to bring a radiation beam into coincidence with each pointing vector. The mechanical positioning systems have mechanical settings corresponding to positions of the LINAC. Geometric beam delivery accuracy is an aspect of any external beam radiation treatment, especially for techniques using high dose gradients and hypofractionation, and can be improved by performing calibration and verification of each mechanical setting of the one or more mechanical positioning systems that position the LINAC.

Calibration of each mechanical setting is defined by the physical design of the delivery system (e.g., LINAC and mechanical positioning systems) and the control systems. To improve accuracy of calibration, device specific measurements may be performed and applied as corrections to an original calibration of the mechanical positioning system or used to replace the original calibration entirely.

Described herein are methods, systems, and phantoms used for radiation-based treatment beam position calibration and verification. A phantom is a device for simulating the in vivo effect of radiation on tissues by absorbing and scattering x-rays in approximately the same way as the tissues of the body. The phantom includes an X-ray luminescent material. In one implementation, a phantom is coated with an X-ray luminescent material. In another implementation, a phantom includes an X-ray luminescent material (e.g., the X-ray luminescent material is integral to the phantom), where at least a portion of the X-ray luminescent material is on the surface of the phantom. One or more optical images of the radiation beam incident on the phantom are used to measure beam pointing offset. The beam pointing offset is calculated from each image, removing the need for a beam scanning procedure. After the beam pointing offset is applied to corresponding mechanical settings, a second image is acquired to measure the effectiveness of the correction (i.e., a verification procedure). The verification procedure can be iterated. The present disclosure is suitable for coplanar and non-coplanar treatment geometries. Implementations of the present disclosure may reduce path calibration time, for example, from about 100 minutes to between 10 and 40 minutes for 100 treatment positions. Extrapolating to a larger set of 1000 treatment positions, the implementations of the present disclosure may require about 2 hours instead of about 17 hours utilizing other methods. Alternatively, other path calibration times may be achieved. In addition to time saving, implementations of the present disclosure may remove uncertainties related to laser-to-radiation-beam coincidence and instantaneous laser intensity variation present in other methods.

FIG. 1 illustrates a calibration system 100 including one or more cameras 110 and a phantom 120 used to calibrate a position of a LINAC 150, in accordance with implementations of the present disclosure.

The LINAC 150 emits a radiation beam 160 at a target (e.g., a phantom 120, a patient, etc.). The LINAC 150 is coupled to a mechanical positioning system 170. The mechanical positioning system 170 positions the LINAC 150 at one or more nodes (e.g., relative to the phantom 120, relative to an isocenter 174 of the mechanical positioning system 170, etc.). The node may include a distance from the phantom 120 and an angle relative to the phantom 120. In one implementation, the mechanical positioning system 170 includes a robotic arm 172 (e.g., with degrees of rotation and translation, robotic manipulator joint rotations system, a frameless robotic radiation therapy system (e.g., CyberKnife® robotic radiosurgery system)). In another implementation, mechanical positioning system 170 includes a gantry-based system 900 (e.g., a C-arm gantry rotation system, LINAC 150 is coupled to a gantry 903 of gantry based system 900 of FIG. 9, etc.). In another implementation, the mechanical positioning system 170 is a helical radiation delivery system 1000 (see FIG. 10). In another implementation, the mechanical positioning system 170 is a couch translation and rotation system. In another implementation, the mechanical positioning system 170 is a gimbal mount measurement system. Alternatively, other types of mechanical positioning systems may be used.

The calibration system 100 includes a camera system 110 having one or more cameras (e.g., camera 110A, camera 110B, etc.), a phantom 120, and a processing device 130.

In one implementation, one or more cameras 110A are coupled to the LINAC 150 (e.g., on a distal end of the LINAC 150 proximate a collimator 152). In another implementation, cameras 110B are located in a static location (e.g., mounted in a location in a treatment room, do not move in response to movement of the LINAC 150). In another implementation, one or more cameras 110 are located on a treatment couch.

In one implementation, the camera system 110 is a visual light camera. In another implementation, the camera system 110 is an infrared camera. In another implementation, the camera system 110 is a charge-coupled device (CCD) camera. In another implementation, the camera system 110 is an intensified CCD (ICCD) camera. In another implementation, the camera system 110 is an electron multiplied ICCD (emICCD) camera (e.g., Princeton Instruments PI-MAX4512 EM). In one implementation, the camera system 110 may be operated in a pulsed mode gated by the radiation beam 160. In another implementation, the camera system 110 is an imaging scintillation or Cerenkov emission detector.

The camera system 110 may be designed to be positioned and shielded to maximize the lifetime of each camera system 110. In one implementation, camera system 110 is positioned at the exit surface of the LINAC 150, to the sides of the treatment beam where camera system 110 will be shielded by the collimator 152. In another implementation, a lens (e.g., Canon EF 135 mm f/2 L USM) of each camera of camera system 110 is positioned adjacent to the collimator 152 and is shielded from the radiation beam 160 by the collimator 152. Each lens may be coupled (e.g., using fiber-optics) to remotely positioned camera electronics (e.g., optics, an image sensor, an intensifier, and so forth), allowing the camera electronics to be positioned at greater distance from the treatment beam. The camera electronics may be positioned in a location where space and weight are less restricted to allow greater radiation shielding to be used that at the exit surface of the LINAC 150. In one implementation, the camera system 110 is integrated (e.g., permanently integrated, non-removably integrated) into the housing 302 (e.g., treatment head) of the LINAC 150. The camera system 110 may additionally be used for one or more of collision avoidance, external patient tracking, entrance patient dosimetry, etc. In another implementation, the camera system 110 is mounted on a removable accessory that attaches to the housing 302 (e.g., head) of the LINAC 150 for calibration. The camera system 110 may be removed during treatment to minimize radiation dose to which the camera system 110 is exposed and may extend the lifetime of the camera system 110.

In one implementation, the phantom 120 is mechanically positioned around a reference point (e.g., positioned around a point in space using a high precision mechanical fixture). The reference point is used in calibration of the mechanical positioning system 170. In one implementation, the reference point is an isocenter 174 (e.g., geometric isocenter) of the mechanical positioning system 170 (e.g., isocenter 174 of LINAC 150). In another implementation, the reference point is a known offset from the isocenter 174. The position of the isocenter 174 of the mechanical positioning system 170 relative to the surface of the phantom 120 will be known from design of the phantom 120 and the method of mechanically positioning the phantom 120. In one implementation, the phantom 120 is mounted on a support 176.

The phantom 120 includes a phantom body 122. In one implementation, the phantom body 122 is hollow and the thickness and material of a hollow phantom body 122 allows transmission of backscattered exit surface image (see FIGS. 3D and 5B). The phantom 120 may have a transparency that allows acquiring, using one camera system 110 at one location, of an image of an entrance feature 360 of a radiation beam 160 entering the phantom 120 and an exit feature 370 of the radiation beam 160 exiting the phantom 120 (see FIG. 3D).

Figure 5A:
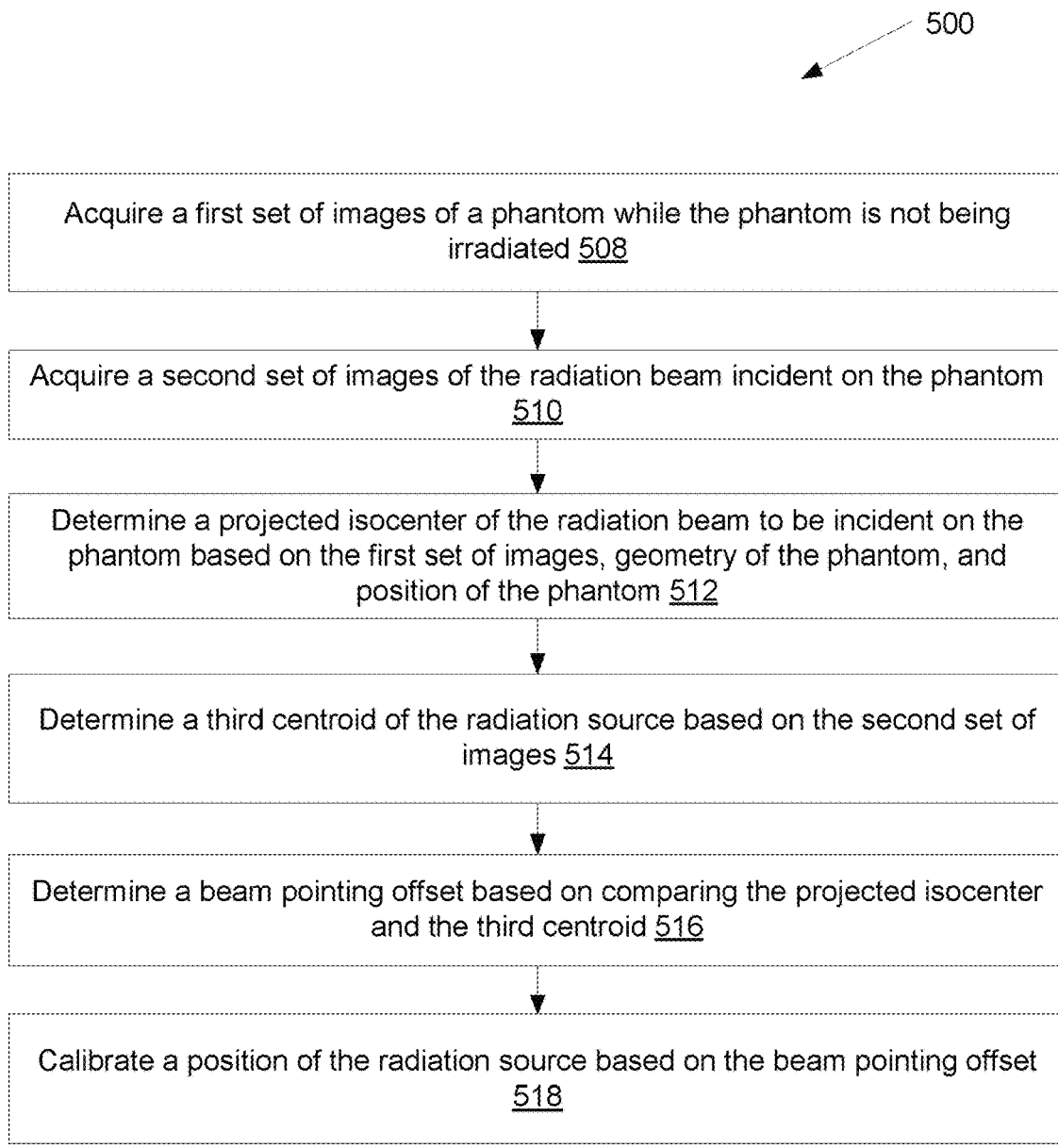
FIG. 5A illustrates a flow diagram of a method for calibration of a position of a LINAC using one or more cameras coupled to the LINAC to acquire images of an entrance surface of the phantom, in accordance with implementations of the present disclosure.
Figure 5B:
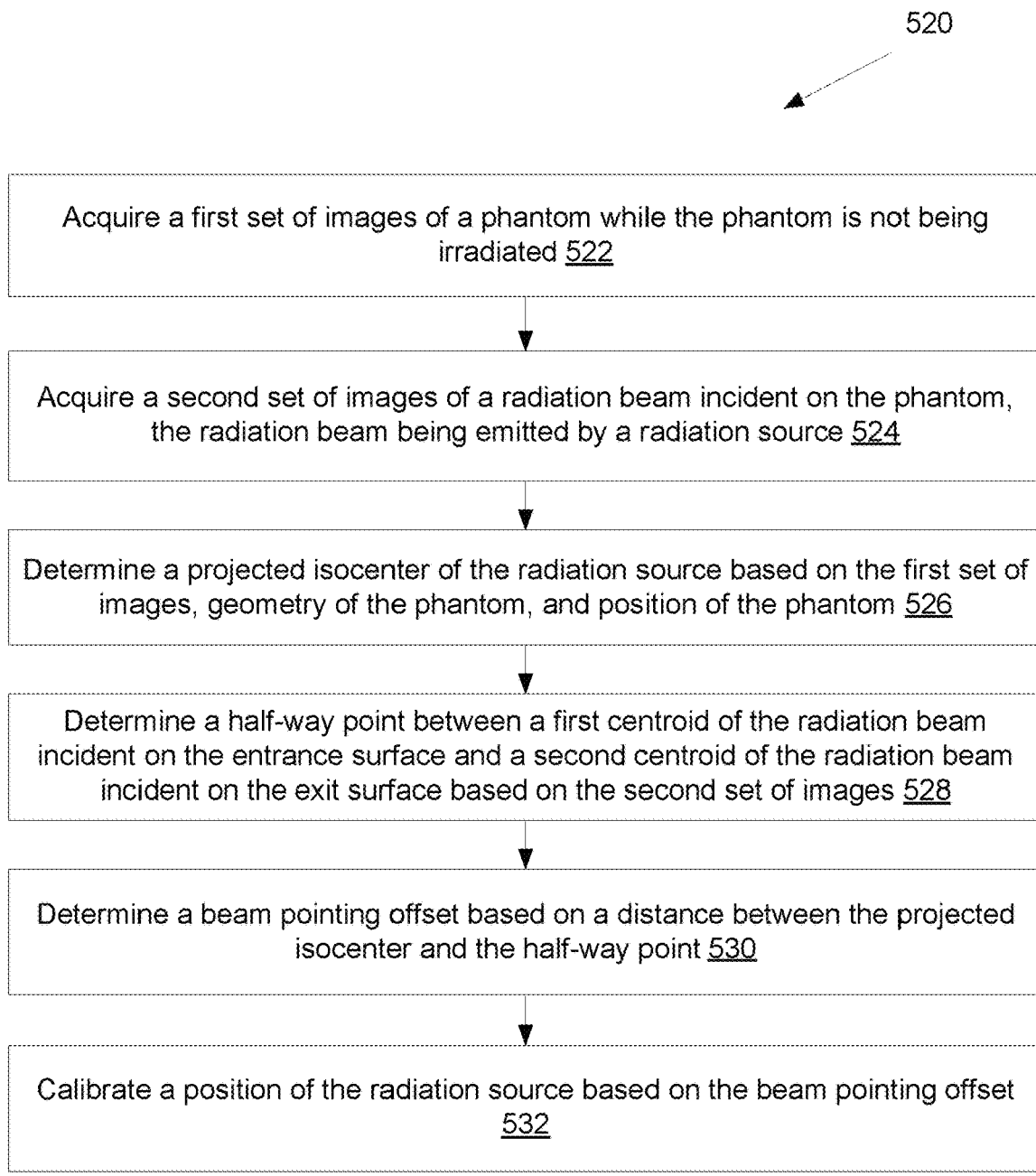
FIG. 5B illustrates a flow diagram of a method for calibration of a position of a LINAC using one or more cameras coupled to the LINAC to acquire images of an entrance surface and an exit surface of the phantom, in accordance with implementations of the present disclosure.
Figure 5C:
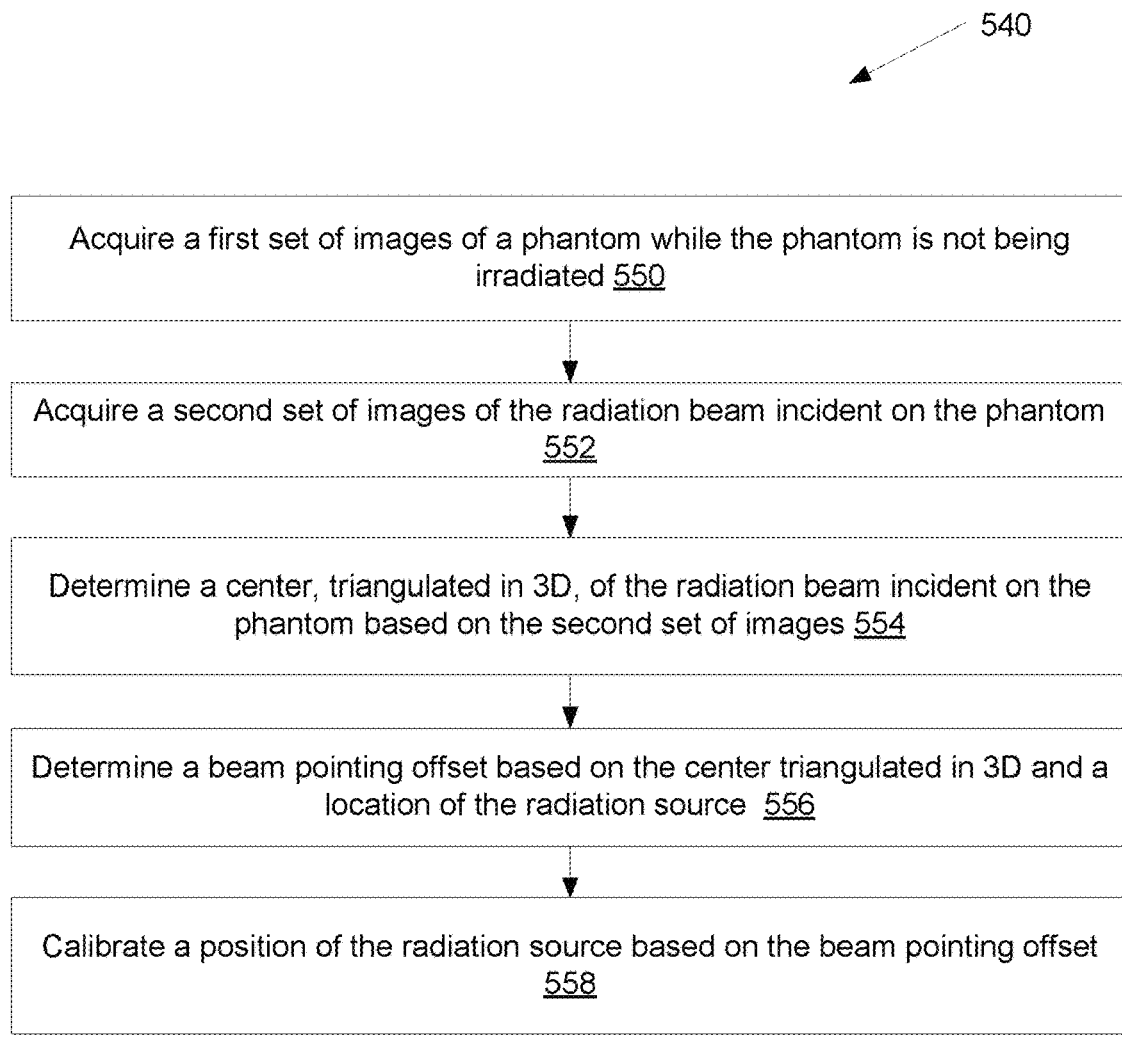
FIG. 5C illustrates a flow diagram of a method for calibration of a position of a LINAC using cameras positioned at static locations to acquire images of an entrance surface of the phantom, in accordance with implementations of the present disclosure.
Figure 5D:
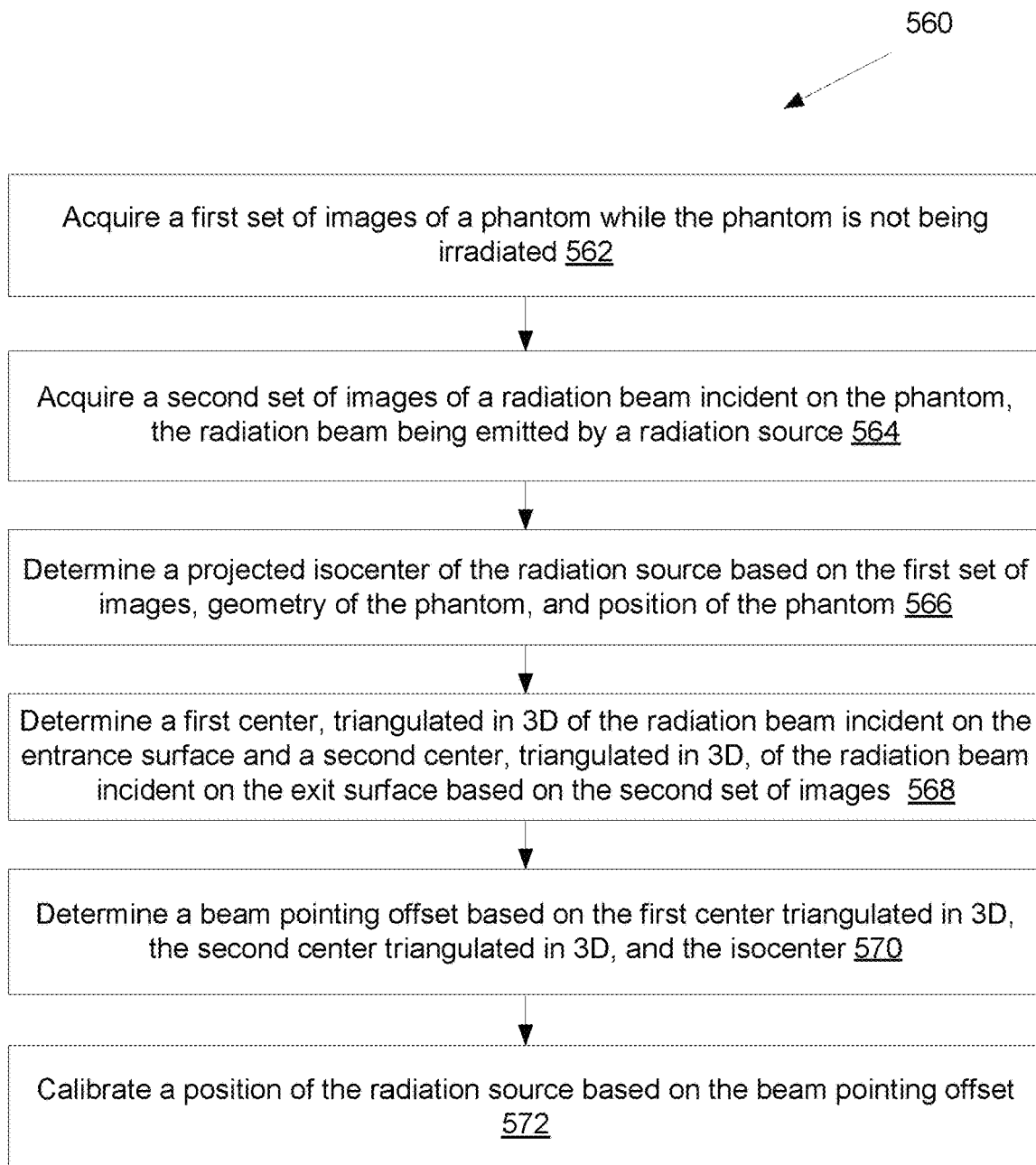
FIG. 5D illustrates a flow diagram of a method for calibration of a position of a LINAC using cameras located at static locations to acquire images of an entrance surface and an exit surface of the phantom, in accordance with implementations of the present disclosure.

In another implementation, the phantom body 122 includes a substrate that is opaque (see FIG. 5D). The opaqueness of the phantom may not allow acquiring, using one camera system 110 at one location, of an image of an entrance feature 360 of a radiation beam 160 entering the phantom 120 and an exit feature 370 of the radiation beam exiting the phantom 120 (see FIG. 3D).

The phantom body 120 includes an X-ray luminescent material 124. In one implementation, the phantom body 122 is coated with an X-ray luminescent material 124. In another implementation, the X-ray luminescent material 124 is at least partially on the surface of the phantom body 122. In another implementation, the X-ray luminescent material 124 is at least partially embedded in the outer layer of the phantom body 122. In another implementation, the X-ray luminescent material 124 is integral to the material of the phantom body 122. For example, the phantom body 122 may include a Terbium activated gadolinium oxysulphide ($Gd_2O_2S_2$) scintillator material 124. In one implementation, the X-ray luminescent material 124 is an X-ray scintillation material with superficial build-up material. In another implementation, the X-ray luminescent material 124 is an X-ray scintillation material without superficial build-up material. In another implementation, the X-ray luminescent material 124 is a dielectric material (e.g., water, plastic, etc.) to generate a Cerenkov optical signal in response to a radiation beam 160 incident on the phantom 120. In one implementation, the dielectric material is doped with a fluorescent compound (e.g., a wavelength shifter) to enhance light emission at a plurality of angles (e.g., most angles of the radiation beam 160 incident to the phantom 120) and to improve detection sensitivity. In another implementation, the dielectric material is not doped with fluorescent compound.

The surface of the phantom 120 is uniform. A relationship of optical signal (e.g., a measurement of a radiation beam incident to the surface) to absorbed dose (e.g., a measurement of absorption of the radiation beam in the phantom) of the radiation beam 160 incident on the phantom 120 is constant over the surface of the phantom 120. The phantom 120 may include a pattern (e.g., checkerboard pattern, see FIG. 2C) of visually identifiable features (e.g., squares of checkerboard pattern) at relative positions overlaid on the X-ray luminescent material 124.

The phantom body 122 may be spherical (see FIG. 2A), cylindrical (see FIG. 2B), cubical, conical, or another shape.

FIG. 2A illustrates a phantom 120A including a spherical phantom body 122A that includes an X-ray luminescent material 124, in accordance with implementations of the present disclosure. In one implementation, for calibration of a mechanical positioning system 170 coupled to a LINAC 150 that emits a radiation beam 160 that is non-coplanar, the phantom body 122A may be spherical and the phantom 120A is centered on the isocenter 174 of the mechanical positioning system 170 (e.g., isocenter 174 of the LINAC 150).

FIG. 2B illustrates a phantom 120B including a cylindrical phantom body 122B that includes an X-ray luminescent material 124, in accordance with implementations of the present disclosure. In one implementation, for calibration of a mechanical positioning system 170 coupled to a LINAC 150 that emits a radiation beam 160 that is coplanar, the phantom body 122B may be cylindrical (i.e., cylindrical phantom body 122B) and includes a first circular end 210 and a second circular end 220 (not shown). A phantom axis 230 is aligned with a first center 212 of the first circular end 210 a second center 222 (not shown) of the second circular end 220. The phantom axis 230 is coincident with an axis of rotation of the LINAC 150.

Figure 2C:
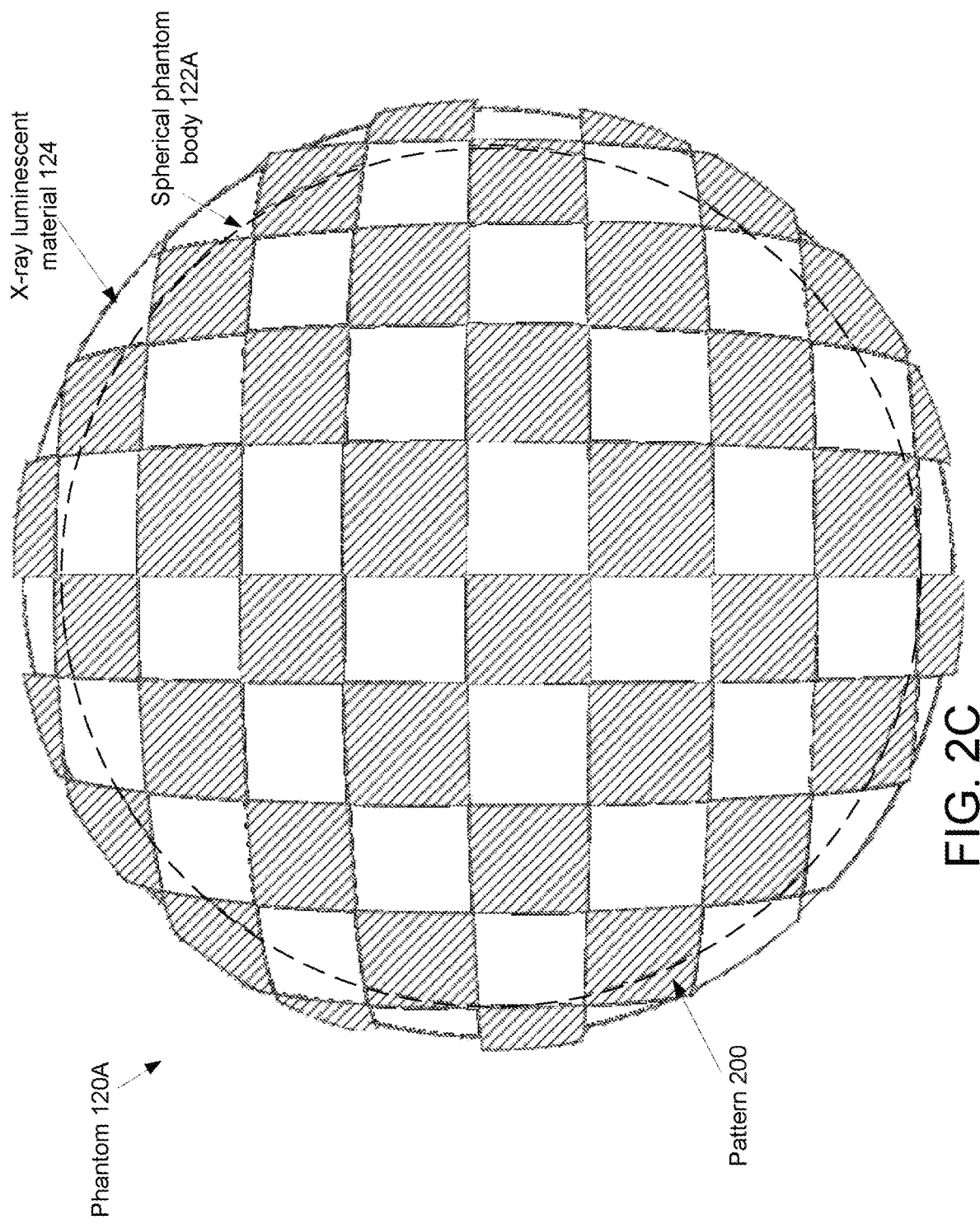
FIG. 2C illustrates a phantom including a spherical phantom body that includes an X-ray luminescent material overlaid with a pattern, in accordance with implementations of the present disclosure.

FIG. 2C illustrates a phantom 120A including a spherical phantom body 122A that includes an X-ray luminescent material 124 and overlaid with a pattern 200, in accordance with implementations of the present disclosure. The pattern 200 is an optical calibration object containing visually identifiable features at known relative positions (e.g., a checkerboard pattern) that is overlaid on the X-ray luminescent material 124 on the outer surface of the phantom body 122. In one implementation, the pattern 200 is used for calculating the pose of the camera with respect to the beam axis 306 of the radiation beam (see method 500 of FIG. 5A and method 540 of FIG. 5C).

Although FIG. 2C illustrates pattern 200 overlaid on a spherical phantom body 122A, pattern 200 can be overlaid on any other shape of phantom body 122. Although a checkerboard pattern is illustrated in FIG. 2C, alternative types of patterns may be used.

Figure 3A:
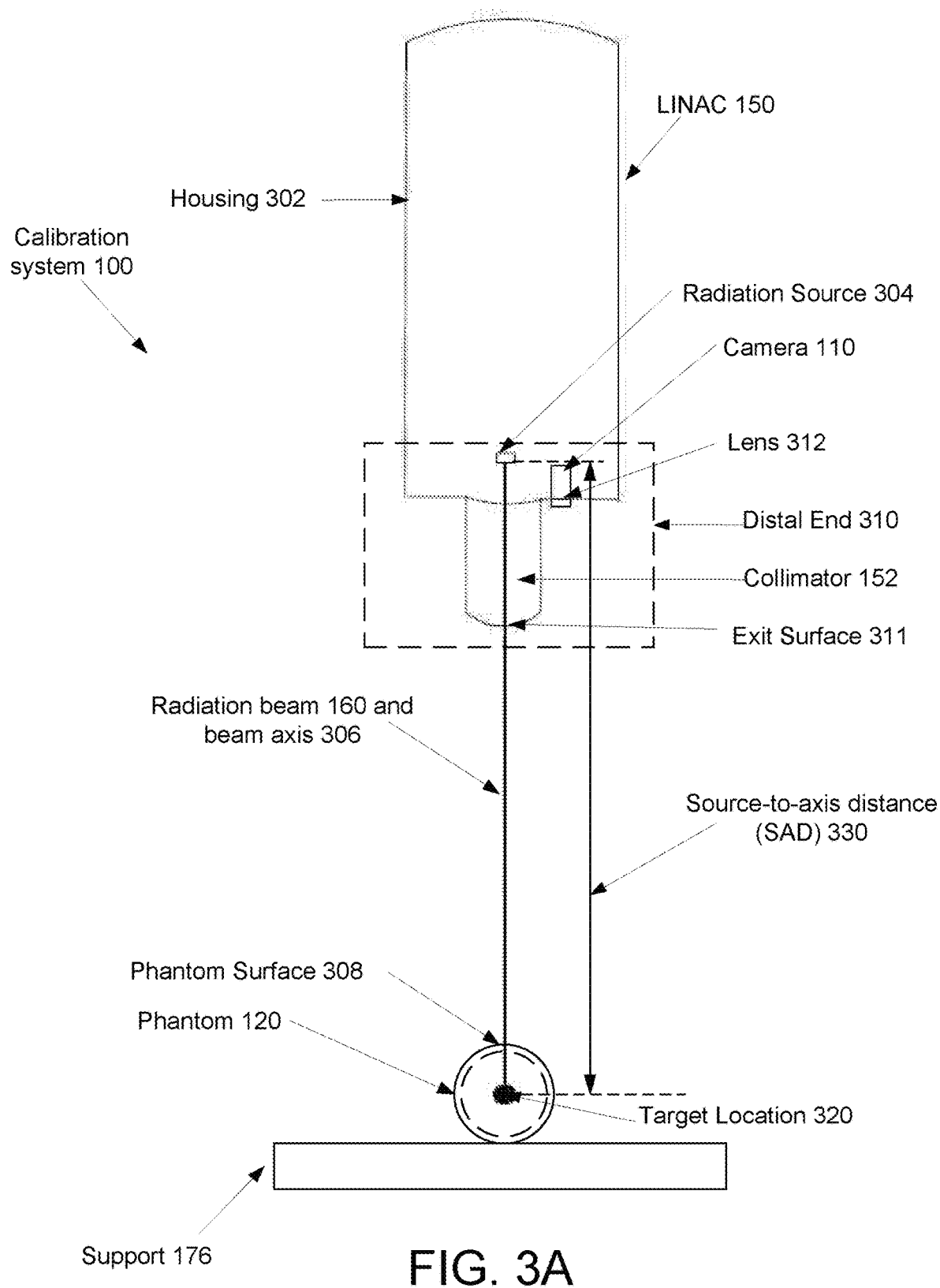
FIG. 3A illustrates a calibration system, in accordance with implementations of the present disclosure.
Figure 3B:
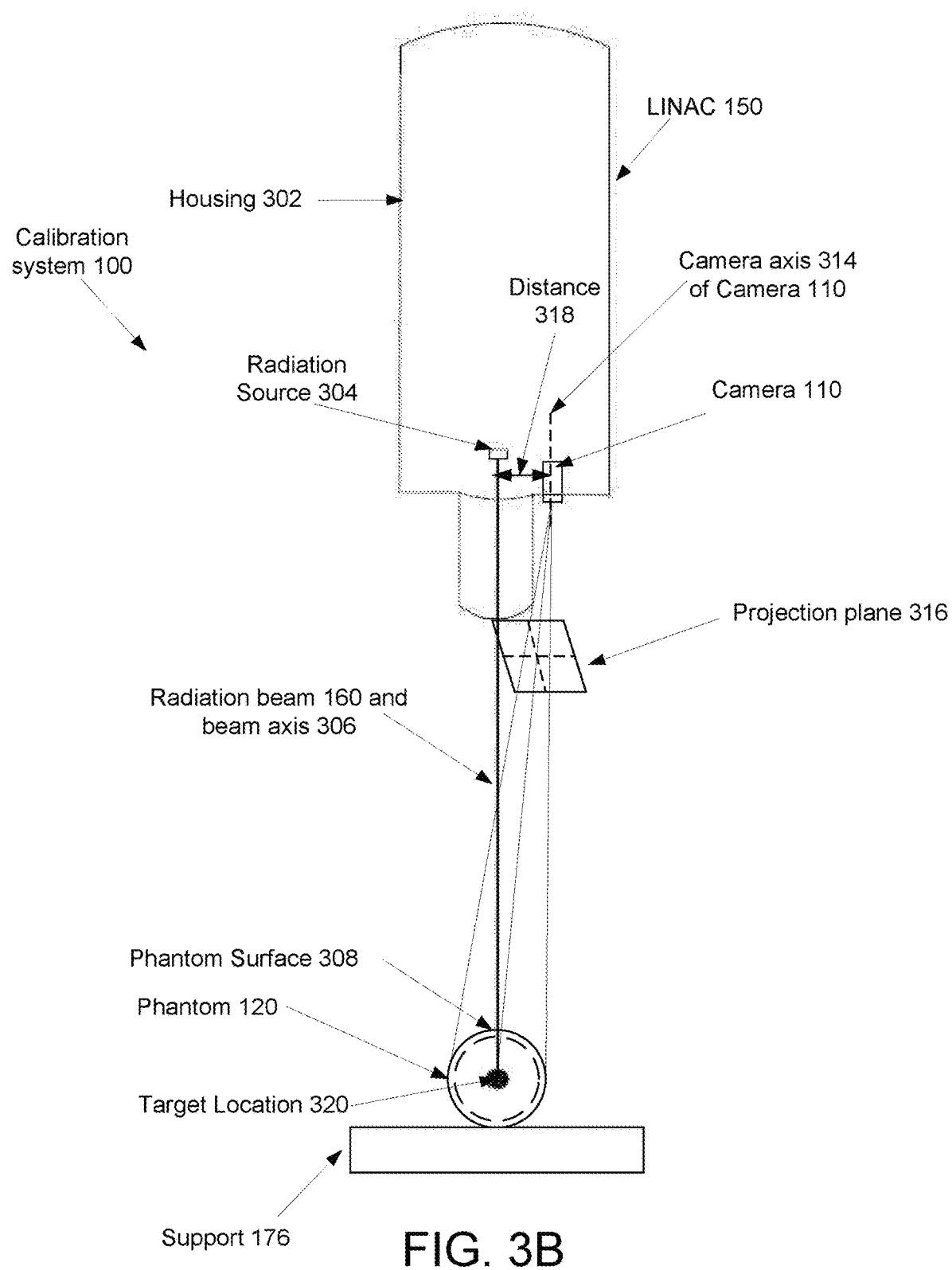
FIG. 3B illustrates incidence of the radiation beam on the phantom compared to view of a camera, in accordance with implementations of the present disclosure.
Figure 3C:
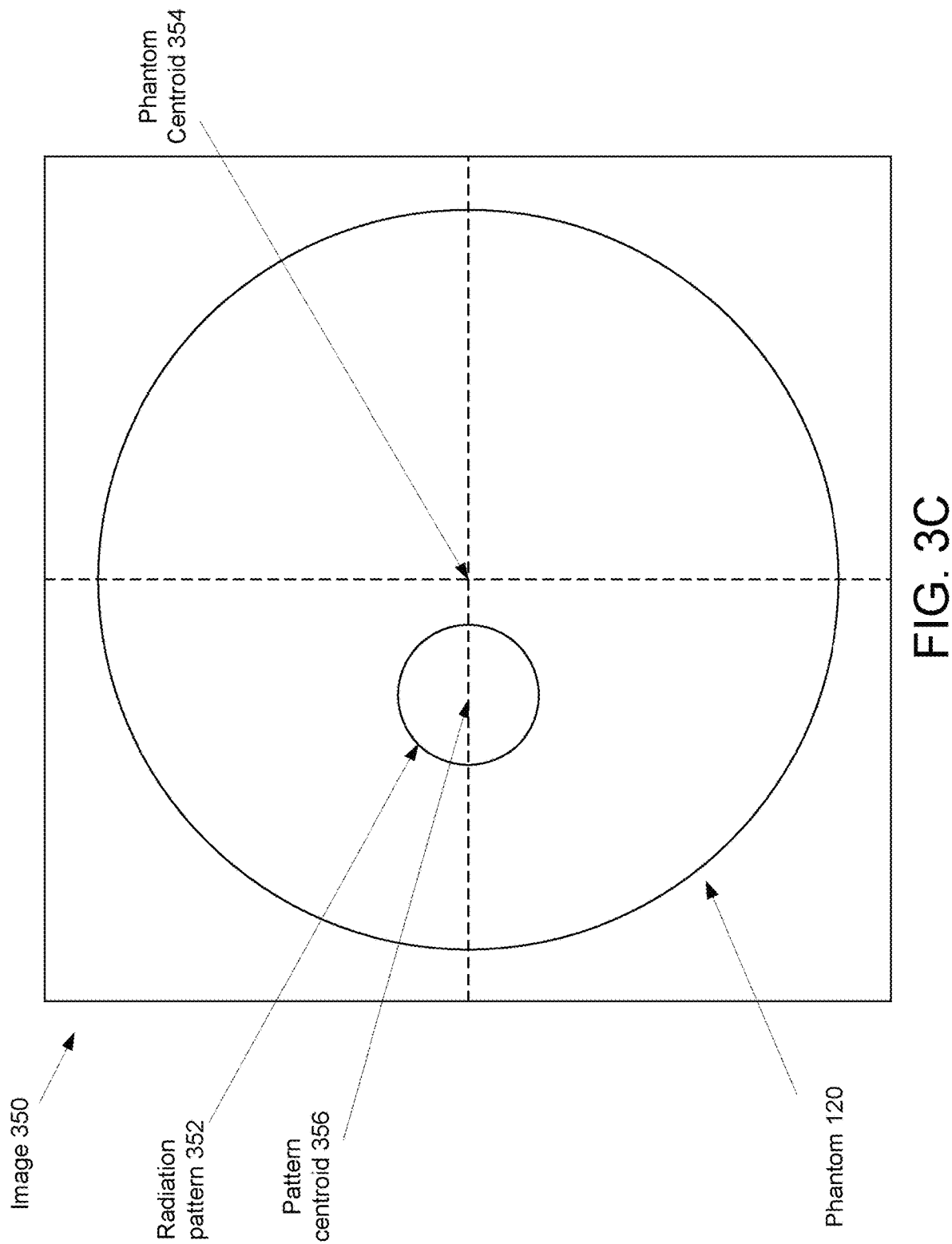
FIG. 3C illustrates the view of a camera of incidence of the radiation beam on the phantom, in accordance with implementations of the present disclosure.
Figure 3E:
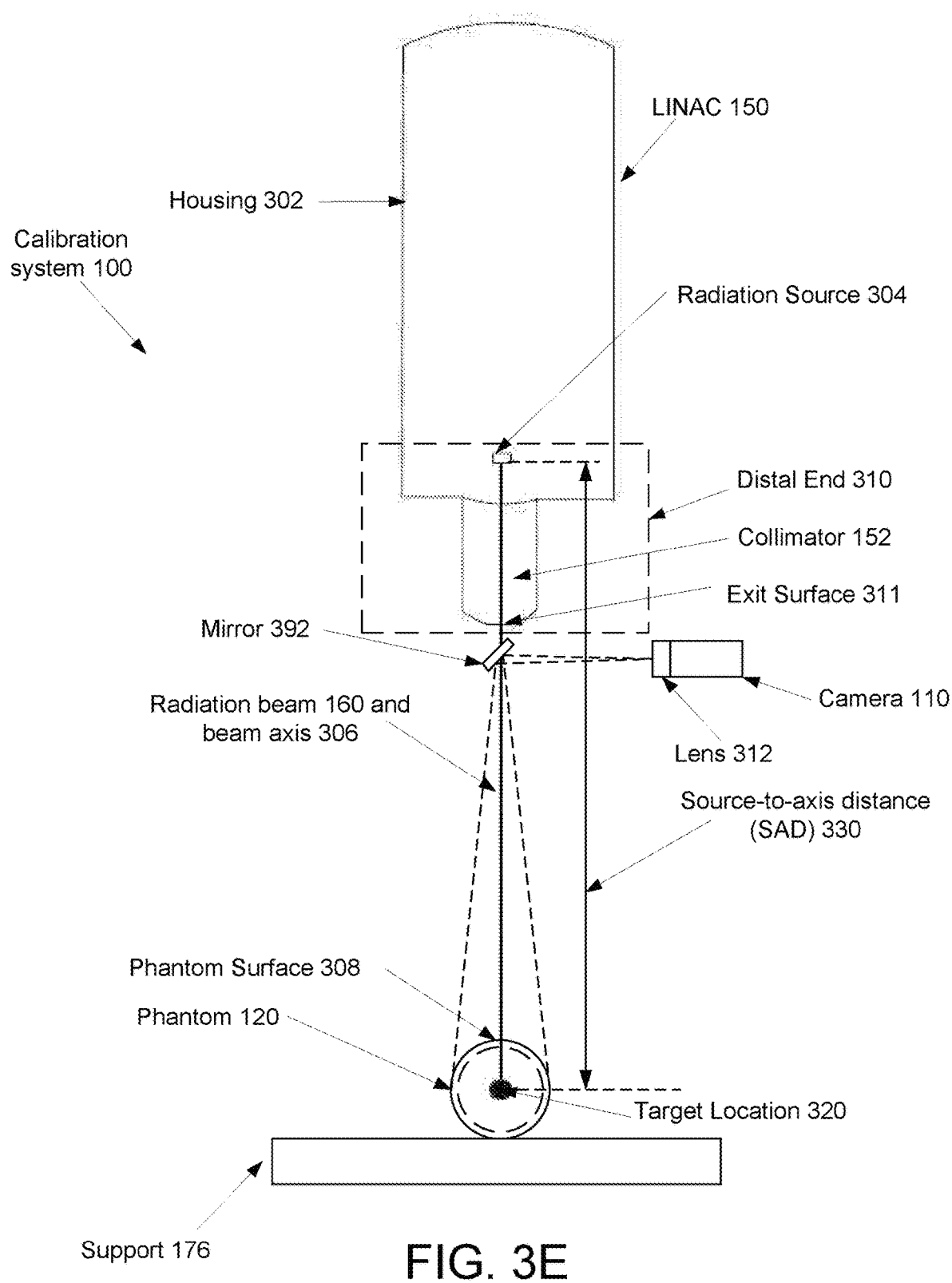
FIG. 3E illustrates a calibration system, in accordance with implementations of the present disclosure.

FIGS. 3A and 3E illustrates a calibration system 100 coupled to a LINAC 150, in accordance with implementations of the present disclosure. The calibration system 100 includes a camera system 110 and a phantom 120. The phantom 120 is radiated by a radiation beam 160 emitted by LINAC 150. The LINAC 150 has a housing 302 coupled to a collimator 152. One or more radiation beams 160 may be emitted from a distal end 310 of the LINAC 150 along one or more beam axes 306 to a target location 320. In one implementation, the target location 320 is located in or on a phantom 120. In another implementation, the target location 320 is located in or on a surface of a patient.

In one implementation, one or more of the beam axes 306 may be substantially normal to the target location 320 (e.g., perpendicular to the phantom surface 308 overlaying the target location, forming a ninety degree beam incident angle 150 with the phantom surface 308). The one or more radiation beams 160 may be emitted through collimation (e.g., an aperture between banks of leaves in the collimator 152, rectangular variable collimation, circular variable collimation, fixed collimation (e.g., cones), etc.).

In one implementation, the distal end 310 of the housing 302 of LINAC 150 may be the radiation source 304. In another implementation, a distal end 310 of the housing 302 of LINAC 150 may be the area proximate where the housing 302 is coupled to the collimator 152. In another implementation, a distal end 310 of the housing 302 of LINAC 150 may be the area proximate where the radiation beam 160 is emitted from the housing 302. In another implementation, the distal end 310 of housing 302 may be where a one or more cameras 110 are coupled to the housing 302.

A source-to-axis distance (SAD) 330 is measured from the radiation source 304 to the target location 320. One or more of the support 176 or LINAC 150 may be used to vary the SAD 330. In one implementation, support 176 is a stage that moves the phantom 120 relative to the LINAC 150 to vary the SAD 330. In another implementation, the support 176 is a couch and motion of the couch alters the SAD 330. In another implementation, support 176 is floor or a wall of a treatment room and a robotic manipulator (e.g., robotic arm 172 of FIG. 1) is used to vary the SAD 330.

In some implementations, the one or more cameras 110 may be coupled to the housing 302 of LINAC 150 at locations that do not interfere with the removal and attachment of the collimator 152. In one implementation, each camera of camera system 110 may be coupled to the housing 302 at a distal end 310 of the LINAC 150. In another implementation, each camera of camera system 110 may include a lens 312 disposed at a distal end 310 of the LINAC 150 proximate exit of the radiation beam 160 from the collimator 152 (e.g., exit surface 311) at a location that does not interfere with removal and attachment of the collimator 152. Each lens 312 may be shielded from the one or more radiation beams 160 by the collimator 152. Each camera of camera system 110 may capture a set of images (e.g., live images) of the radiation beam 160 incident to the phantom 120 (e.g., optical Cerenkov emission generated at the phantom 120 by charged particles of the radiation beam 160 moving in a medium of the phantom 120 with a phase speed greater than the speed of light in the medium).

As shown in FIG. 3E, in some implementations, the one or more cameras 110 may be positioned at an angle (e.g., 90 degrees) relative to the beam axis 306. The one or more cameras 110 may be disposed proximate the distal end 310 of housing 302. In one implementation, the one or more cameras 110 are coupled to the housing 302. In another implementation, the one or more cameras 110 are not coupled to the housing. In some implementations, the camera system 110 and the radiation beam 160 have in-line geometry along the beam axis 306. The in-line geometry (e.g., shared axis) may be achieved using a mirror 392. The mirror 392 may be in the beam path of the radiation beam 160. The camera system 110 may be disposed at an angle (e.g., 90 degrees) relative to the beam axis 306 and a mirror 392 (e.g., a 45-degree mirror) may be used to align the optical axis and the beam axis 306. The mirror 392 may be calibrated (e.g., a one-time calibration) to provide aligning of the optical axis and the beam axis 306.

In one implementation, an image of the radiation beam 160 incident on the phantom 120 may be acquired with a phantom 120 including a scintillator material (e.g., a Terbium activated $Gd_2O_2S_2$ scintillator material) at least partially on the surface of the phantom 120, using 5 monitor units (MUs) (a measure of machine output from a LINAC 150) with a 6× radiation beam 160 (e.g., photon beam produced by the acceleration of electrons to 6 megaelectron-volts (MeV)) at approximately 1000 millimeter (mm) SAD 330, and with no build-up. This may result in approximately 0.5 seconds per image acquisition and allowing an additional 2.5 seconds for optical image acquisitioning and processing. This is approximately ten times faster than other calibration and verification methods (excluding robot motion time). In another implementation, perspective correction is used, resulting in 30 minutes of perspective calibration followed by 100 nodes at 3 seconds per node for calibration, followed by verification, so the total time with the methods disclosed herein would be 40 minutes (excluding robot traversal) instead of 100 minutes with the other calibration and verification methods. For calibration and verification of 1,000 nodes (e.g., for a dynamic treatment delivery method of delivering radiation beams from a continuous range of beam source locations around the patient), the same comparison becomes approximately 2 hours by the methods disclosed herein instead of 17 hours by other methods.

FIG. 3B illustrates incidence of the radiation beam 160 on the phantom 120 compared to view of a camera system 110, in accordance with implementations of the present disclosure.

The LINAC 150 emits a radiation beam 160 from the radiation source 304 to the target location 320 in or on the phantom 120. The camera system 110 acquires an image of the radiation beam 160 incident on the phantom 120 at the phantom surface (e.g., radiation pattern 352 on entrance surface in FIG. 3C). Camera system 110 has a camera axis 314 (e.g., center of lens 312 of camera 110, center of the image acquired by the camera, center of the projection plane 316, etc.) and radiation beam 160 has a beam axis 306 (e.g., center of the radiation beam 160). In one implementation, the camera axis 314 and beam axis 306 may both intersect the phantom 120 at the target location 320 (e.g., at the center of the phantom 120).

The camera 110 is not coincident with the beam axis 306 of radiation beam 160. The camera system 110 has a camera pose including translation (e.g., distance 318 between camera axis 314 and beam axis 306) and rotation (e.g., angle of camera axis 314 in relation to beam axis 306). The distance 318 between a camera axis 314 of the camera system 110 and the beam axis 306 results in a shift between the phantom centroid 354 of the phantom 120 and the pattern centroid 356 of a radiation pattern 352 (e.g., radiation scintillation pattern) in images acquired by camera system 110 (see image 350 of FIG. 3C). A projection plane 316 is a view of the camera system 110 of the phantom 120 and a radiation pattern 352 the phantom surface 308. The projection plane 316 corresponds with an image 350 acquired by camera system 110 (see FIG. 3C).

FIG. 3C illustrates the view of a camera system 110 of a radiation pattern 352 from the incidence of the radiation beam 160 on the phantom 120, in accordance with implementations of the present disclosure. Image 350 is an image of the phantom 120 and radiation pattern 352 as acquired by camera system 110. The phantom centroid 354 of the phantom 120 (e.g., center of a spherical phantom) and the pattern centroid 356 of the radiation pattern 352 in image 350 do not coincide because of the distance 318 and angle between the beam axis 306 and the camera axis 314, and the finite size of the phantom. The offset between the phantom centroid 354 and the pattern centroid 356 can be modeled based on the camera pose (e.g., translation and rotation of camera system 110) relative to the phantom 120.

FIG. 3D illustrates radiation luminescence generated at an entrance surface and an exit surface of the phantom 120, in accordance with implementations of the present disclosure.

In one implementation, the phantom 120 may be constructed so that both entrance feature 360 and exit feature 370 are visible in the same projection (e.g., projection plane 316, each of the first set of images is of an entrance surface and an exit surface of the phantom 120, etc.). For example, a camera system 110 may acquire an image of the phantom 120, where the image displays both the entrance feature 360 and the exit feature 370. The thickness and material of the phantom 120 allow transmission of backscattered exit surface image. In one implementation, the entrance feature 360 and the exit feature 370 are separated in an image by the dimensions of the phantom 120 being greater than a first threshold size and the radiation beam 160 being less than a second threshold size. The material and thickness of the phantom 120 may separate the entrance feature 360 and exit feature 370 by optical intensity.

In another implementation, two or more images are acquired by one or more cameras of camera system 110 in different locations (e.g., a camera 110 in a first location and a second location, or a first camera 110 in a first location and a second camera in a second location). In one implementation, the position of the entrance feature 360 or exit feature 370 of the phantom 120 relative to the array of cameras 110 is triangulated using a first orientation of a first image from a first camera 110 and a second orientation of a second image from a second camera. The position of the entrance feature 360 or exit feature 370 relative to the radiation beam 160 may be triangulated using a first orientation of a first image from a first camera 110 and a second orientation of a second image from a second camera. The phantom 120 may be an opaque substrate.

One or more images (or views via camera 110) of the phantom 120 may be of the radiation beam 160 incident on the entrance surface and exit surface of the phantom 120. The radiation beam 160 incident on the entrance surface of the phantom 120 generates an entrance feature 360 (e.g., a teardrop shape) and the radiation beam 160 incident on the exit surface of the phantom 120 (e.g., exiting the phantom 120) generates an exit feature 370 (e.g., a teardrop shape). The entrance feature 360 has a first centroid 362 and the exit feature 370 has a second centroid 372. The first centroid 362 and the second centroid 372 create a line 380 through the phantom and the line 380 has a half-way point 382. A distance between the half-way point 382 and the center 384 of the phantom 120 is the beam pointing offset 390.

In one implementation, the center 384 of the phantom 120 may be a projected isocenter of the LINAC 150 based on first images of the phantom 120 while the phantom 120 is not being irradiated, geometry of the phantom 120, and position of the phantom 120. The half-way point 382 between the first centroid 362 and the second centroid 372 is based on second images of the phantom 120 while the radiation beam 160 is incident on the phantom 120. The lighting may be turned off or dimmed during the acquisition of images of the phantom 120 with the phantom is being irradiated and the lighting may be turned on during the acquisition of images of the phantom 120 while the phantom 120 is not being irradiated.

In one implementation, lighting is constant (e.g., one room lighting state for the whole procedure) and a camera system 110 captures one image that includes both the outline of the phantom 120 and the scintillation or Cerenkov signal. A beam pointing offset is determined from the image and a position of the radiation source (e.g., LINAC 150) is calibrated based on the beam pointing offset.

In one implementation, using one or more cameras of camera system 110 coupled to the LINAC 150, images are acquired of an entrance feature 360 and no exit feature 370 (see FIG. 5A). In another implementation, using one or more cameras of camera system 110 coupled to the LINAC 150, images are acquired of an entrance feature 360 and an exit feature 370 (see FIG. 5B). In another implementation, using camera system 110 located in static positions, images are acquired of an entrance feature 360 and no exit feature 370 (see FIG. 5C). In another implementation, using camera system 110 located in static positions, images are acquired of an entrance feature 360 and an exit feature 370 (see FIG. 5D).

Figure 4:
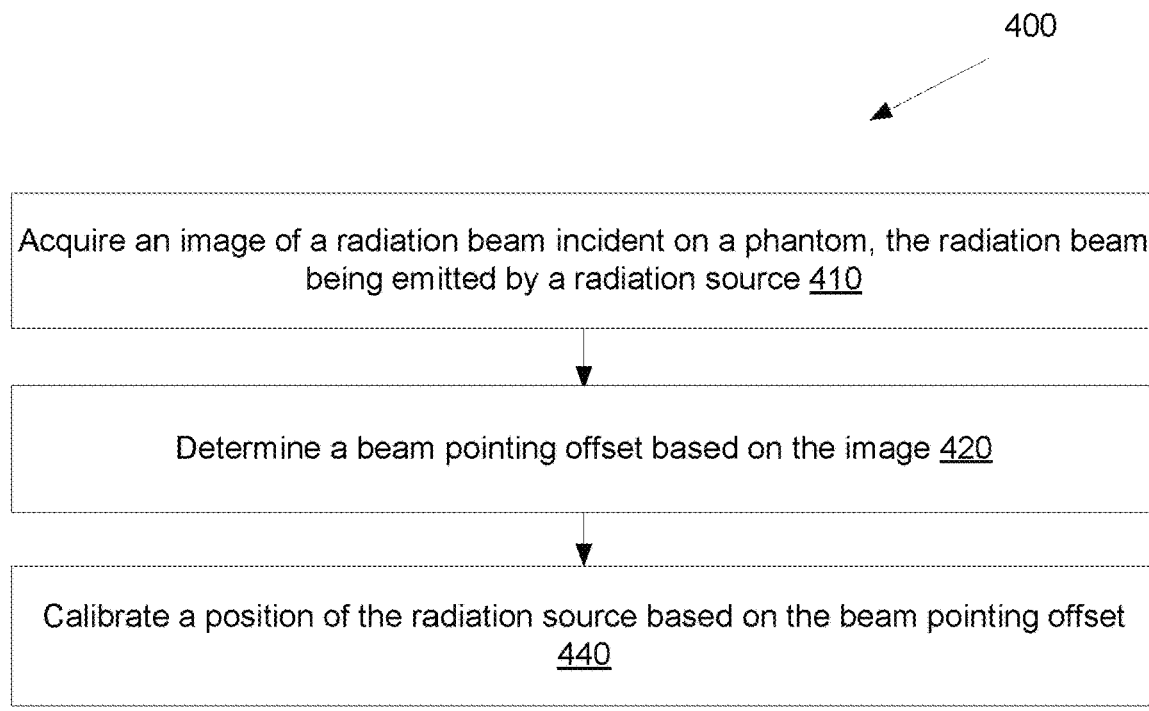
FIG. 4 illustrates a flow diagram of a method for calibration of a position of a LINAC, in accordance with implementations of the present disclosure.
Figure 6:
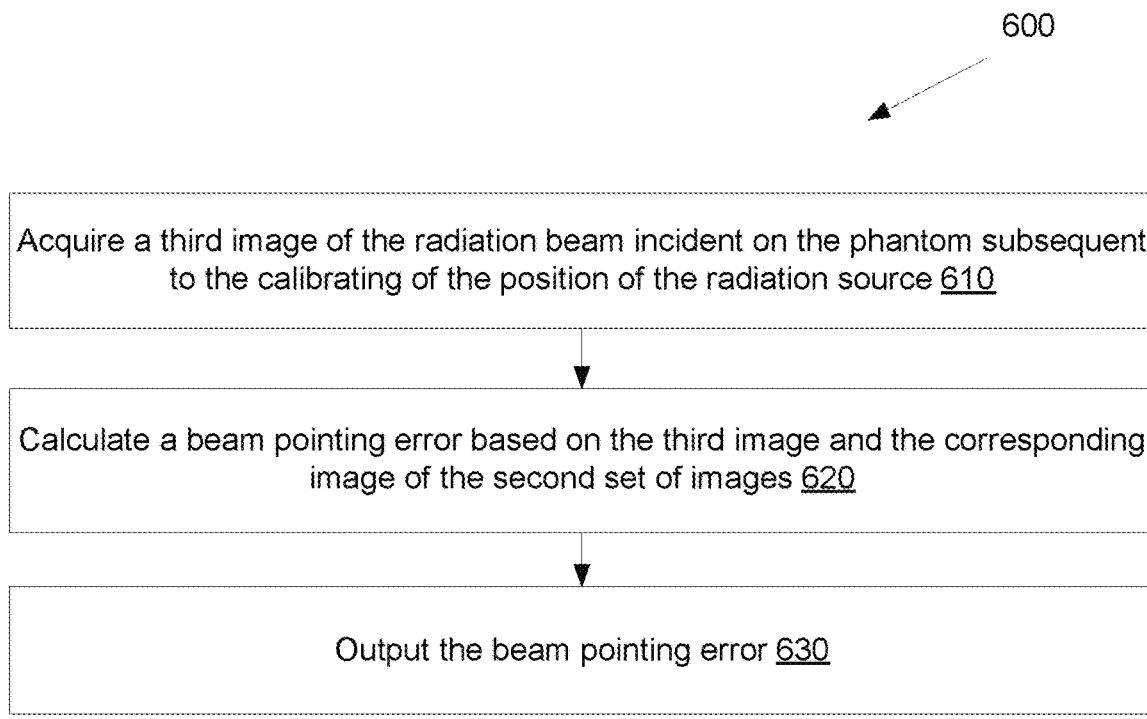
FIG. 6 illustrates a flow diagram of a method for verification of a position of a LINAC in accordance with implementations of the present disclosure.

FIGS. 4-5D illustrate flow diagrams of methods 400, 500, 520, 540, and 560 for calibration of a position of a LINAC 150, in accordance with implementations of the present disclosure. FIG. 6 illustrates a flow diagram of method 600 for verification of a position of a LINAC 150, in accordance with implementations of the present disclosure. Methods 400, 500, 520, 540, 560, and 600 are described in relation to the calibration or verification of a position of a LINAC 150. However, it should be understood that methods 400, 500, 520, 540, 560, and 600 may also be used to calibrate or verify a position of other systems that emit radiation, in particular, a radiation beam 160. The methods 400, 500, 520, 540, 560, and 600 may be performed by processing logic that comprises hardware (e.g., circuitry, dedicated logic, programmable logic, microcode, etc.), software (e.g., instructions run on a processing device to perform hardware simulation), or a combination thereof.

In one implementation, prior to any of the methods in FIGS. 4-5D, intrinsic properties (e.g., intrinsic camera properties, sensor distortions, lens distortions, etc.) of the one or more cameras of camera system 110 are determined. This is a one-off procedure that may be performed prior to installation of the one or more cameras of camera system 110 (e.g., prior to coupling one or more cameras 110 to the LINAC 150, prior to locating the cameras of camera system 110 in stationary locations relative to the phantom 120, etc.). Corrections for the distortions in the intrinsic properties of the camera system 110 are applied to all images described in FIGS. 4-5D. For example, the processing device applies corrections for the sensor and lens distortions to the first set of images and the second set of images.

FIG. 4 illustrates a flow diagram of a method 400 for calibration of a position of a LINAC 150, in accordance with implementations of the present disclosure.

At block 410, processing logic acquires, using a camera system 110, an image of a radiation beam 160 incident on a phantom 120. In one implementation, block 410 includes acquiring, using one or more cameras of camera system 110, a first set of images of a phantom 120 while the phantom 120 is not being irradiated and acquiring, using one or more cameras of camera system 110, a second set of images of a radiation beam 160 incident on the phantom. The phantom 120 includes an X-ray luminescent material 124 at least partially on the surface of the phantom body 122. The radiation beam 160 is emitted by a radiation source (e.g., a LINAC 150).

At block 420, processing logic determines a beam pointing offset based on the image. In one implementation, block 410 includes determining the beam pointing offset based on the first set of images and the second set of images.

At block 440, processing logic calibrates a position of the LINAC 150 based on the beam pointing offset. In some implementations, the beam pointing error from block 630 of FIG. 6 may be applied as a beam pointing offset to mechanical beam positioning devices (e.g., devices of mechanical positioning system 170) to adjust the position of the LINAC 150. The calibration method of any one of methods 400, 500, 520, 540, or 560 and the verification method of method 600 may be iterated. A list of beam pointing offsets that can be applied by the mechanical positioning systems during treatment (e.g., used to amend or replace the existing pointing calibration) may be output (e.g., as a report).

Blocks 410-440 may be repeated (e.g., after block 440, the method 400 may restart at 410) if a set of a radiation beams is to be calibrated.

FIGS. 5A-D illustrate flow diagrams for calibration of a position of a radiation source using one or more cameras of camera system 110 coupled to the radiation source. In one implementation, the methods of FIGS. 5A-D include one camera of system 110 acquiring one image of the radiation beam incident on the phantom 120, a beam pointing offset being determined based on the image, and the position of the radiation source being calibrated based on the beam pointing offset. In another implementation, the methods of FIGS. 5A-D include one or more cameras acquiring a plurality of images of the radiation beam incident on the phantom 120, a beam pointing offset being determined based on the plurality of images, and the position of the radiation source being calibrated based on the beam pointing offset.

FIG. 5A illustrates a flow diagram of a method 500 for calibration of a position of a LINAC 150 using one or more cameras of camera system 110 coupled to the LINAC 150 to acquire images of an entrance surface of the phantom 120, in accordance with implementations of the present disclosure.

At block 508, processing logic acquires, using one or more cameras of camera system 110, a first set of images of a phantom while the phantom 120 is not being irradiated. The phantom 120 may be mounted at the isocenter 174 of the mechanical positioning system 170 (e.g., isocenter 174 of the LINAC 150).

At block 510, processing logic acquires, using the one or more cameras of camera system 110, a second set of images of the radiation beam 160 incident on the phantom. The second set of images may be of the radiation beam 160 incident on a portion of the phantom surface 308 of phantom 120 that is most proximate to the radiation source 304 (e.g., the entrance feature 360). The radiation beam 160 is collimated to be symmetric about the beam axis 306 (e.g., using a fixed circular collimator).

At block 512, processing logic determines a projected isocenter of the radiation source (e.g., LINAC 150) based on the first set of images, geometry of the phantom 120, and position of the phantom 120. For example, for a phantom 120A with a spherical phantom body 122A that is surrounding the isocenter 174 of the mechanical positioning system 170, the projected isocenter (e.g., phantom centroid 354) is the center 384 of the circular outline of the phantom 120A.

At block 514, processing logic determines a third centroid of the radiation beam 160 incident on the phantom 120 (e.g., pattern centroid 356) based on the second set of images.

At block 516, processing logic determines a beam pointing offset based on comparing the projected isocenter and the third centroid. The processing logic determines a direction of the beam pointing offset. In one implementation, the direction is found by an iterative search. The robot pointing is adjusted by the offset magnitude (e.g., the targeting location 320 is shifted by the magnitude of the beam pointing offset and the location of the radiation source 304 is not adjusted) and the beam pointing offset is applied in a random direction or is guided by the shape of the projected beam aperture onto the phantom surface 308 (e.g., for a circular radiation beam 160 projected onto a spherical phantom body 122A, the beam pointing offset should be applied along the major axis of the projected shape, in the direction of the fat end of the tear drop shape (entrance feature 360)). In another implementation, the direction is found by optical fiducial marks placed on the surface of the phantom 120 from which the orientation of the phantom 120 in room space can be calculated in each optical image which allows the direction of the beam pointing offset to be calculated as well as the magnitude. In another implementation, the direction is found by camera extrinsic parameters (e.g., pose of the camera 110) that describe the orientation of the image relative to the radiation beam 160 and if the nominal orientation of the radiation beam 160 with respect to the room is also known, then the camera extrinsic parameters and the nominal orientation of the radiation beam 160 can be combined to give the offset direction.

At block 518, processing logic calibrates a position of the LINAC based on the beam pointing offset and the relationship. In one implementation, the calibrating the position of the LINAC 150 may be by storing the beam pointing offset for later use. In another implementation, the calibrating the position of the LINAC 150 may be by adjusting the position of the LINAC 150 via the mechanical positioning system 170.

In some implementations, the beam pointing error from block 630 of FIG. 6 may be applied as a beam pointing offset to mechanical beam positioning devices (e.g., devices of mechanical positioning system 170) to adjust the position of the LINAC 150. The calibration method of any one of methods 400, 500, 520, 540, or 560 and the verification method of method 600 may be iterated. A list of beam pointing offsets that can be applied by the mechanical positioning systems during treatment (e.g., used to amend or replace the existing pointing calibration) may be output (e.g., as a report).

Blocks 508-518 may be repeated (e.g., after block 518, the method 500 may restart at 508) if a set of a radiation beams is to be calibrated.

In one implementation, the one or more cameras of camera system 110 are in-line with the beam axis of the radiation beam 160. In another implementation, the one or more cameras are not in-line with a beam axis of the radiation beam and the method further includes calculating pose of the one or more cameras of camera system 110 with respect to the radiation beam axis (e.g., blocks 502-506, not shown in FIG. 5A). At block 502, processing logic acquires, using the one or more cameras of camera system 110, a third set of images of a pattern 200 (see FIG. 2C) overlaid on the X-ray luminescent material 124 while the phantom 120 is not being irradiated. The third set of images is acquired at one or more SAD 330. The one or more SAD 330 may be provided by phantom 120 being mounted on support 176 and the support 176 or LINAC 150 moving relative to each other. Processing logic determines pose (e.g., translation and rotation of camera axis 314 relative to beam axis 306) and focal length of the one or more cameras of camera system 110 from the third set of images of pattern 200.

At block 504, processing logic acquires, using the one or more cameras, a fourth set of images of the radiation beam incident on the pattern at one or more SAD 330 (see FIG. 3A). Processing logic determines a location of the beam axis 306 with respect to the pattern 200 from the fourth set of images. One or more SAD 330 in block 504 may correspond with the one or more SAD in block 502. Each of the third set of images corresponds to one or more images of the fourth set of images.

At block 506, processing logic determines, based on the pose, the focal length, and the location of the beam axis, a relationship between a first centroid of the phantom 120 (e.g., phantom centroid 354 of FIG. 3C) and a second centroid of the radiation beam 160 (e.g., pattern centroid 356 of FIG. 3C) incident on the pattern 200 (e.g., scintillation pattern as seen by the camera). Since the camera axis 314 is not coincident with the beam axis 306, an image 350 of phantom 120 and the radiation pattern 352 will not be concentric even when the radiation beam 160 is pointing exactly at the center of the phantom 120 (e.g., phantom centroid 354). In one implementation, the relationship determined by block 506 may be an expected offset (e.g., distance between phantom centroid 354 and pattern centroid 356 of FIG. 3C) and may be used as a goal (e.g., target value) during determining of the beam pointing offset. In another implementation, the relationship determined by block 506 may be an expected offset (e.g., distance between phantom centroid 354 and pattern centroid 356) may be converted into a beam pointing offset such that the phantom 120 and radiation patterns 352 become concentric in the image 350 acquired by camera system 110 by application of the beam pointing offset.

In one implementation, blocks 502-506 may be a camera calibration setup that is a one-off procedure (if pose is repeatable). In another implementation, blocks 502-506 may be required before each calibration procedure (e.g., blocks 508-518) or verification procedure (e.g., method 600) is performed. In one implementation, blocks 502-506 may be generalized to multiple camera configurations and the accuracy of the calibration may improve with multiple cameras for camera system 110.

FIG. 5B illustrates a flow diagram of a method 520 for calibration of a position of a LINAC 150 using one or more cameras of camera system 110 coupled to the LINAC 150 to acquire images of an entrance surface and an exit surface of the phantom 120, in accordance with implementations of the present disclosure.

Method 520 does not require pose information of the camera system 110 (e.g., does not require blocks 502-506 of method 500).

At block 522, processing logic acquires, using one or more cameras of system 110, a first set of images of a phantom 120 while the phantom 120 is not being irradiated.

At block 524, processing logic acquires, using the one or more cameras of system 110, a second set of images of a radiation beam 160 incident on the phantom 120. Each of the second set of images is of the radiation beam incident on an entrance surface and an exit surface of the phantom (e.g., display both entrance feature 360 and exit feature 370 (see FIG. 3D)). In one implementation, the phantom 120 used in method 500 may be constructed so that both entrance feature 360 and exit feature 370 are visible in the same projection (e.g., projection plane 316, each of the first set of images is of an entrance surface and an exit surface of the phantom 120, etc.). In another implementation, two or more of the first set of images are a super-position of an entrance and an exit surface of the phantom 120. The thickness and material of the phantom 120 allow transmission of backscattered exit surface image. In one implementation, the entrance feature 360 and the exit feature 370 are separated in an image by the phantom 120 having a first size greater than a first threshold size and the radiation beam 160 having a second size less than a second threshold size. The material and thickness of the phantom 120 may separate the entrance feature 360 and exit feature 370 by optical intensity.

At block 526, processing logic determines a projected isocenter of the LINAC 150 onto an image plane based on the first set of images, geometry of the phantom, and position of the phantom. The projected isocenter of the LINAC 150 may be coincident with the center of the phantom. The projected isocenter of the LINAC 150 may be a property of the treatment device as a whole and not of each individual radiation beam 160. For example, the projected isocenter may be the center 384 of phantom 120 that has a spherical phantom body 122A (see FIG. 3D).

At block 528, processing logic determines a half-way point 382 between a first centroid 362 of the radiation beam 160 incident on the entrance surface (e.g., entrance feature 360) and a second centroid 372 of the radiation beam 160 incident on the exit surface (e.g., exit feature 370) based on the second set of images.

At block 530, processing logic determines a beam pointing offset 390 based on a distance between the projected isocenter (e.g., center 384 of phantom 120) and the half-way point 382.

In one implementation, the direction of the beam pointing offset 390 may be determined by an iterative search as described above. In another implementation, the direction of the beam pointing offset 390 may be determined by optical fiducial marks placed on the surface of the phantom 120 as described above.

At block 532, processing logic calibrates a position of the LINAC 150 based on the beam pointing offset.

Blocks 522-532 may be repeated (e.g., after block 532, the method 520 may restart at 522) if a set of a radiation beams is to be calibrated.

FIG. 5C illustrates a flow diagram of a method 540 for calibration of a position of a LINAC 150 using cameras of camera system 110 positioned at static locations to acquire images of an entrance surface of the phantom 120, in accordance with implementations of the present disclosure.

At block 550, processing logic acquires, using one or more cameras of system 110, a first set of images of a phantom 120 while the phantom 120 is not being irradiated. In one implementation, the phantom 120 is located about the isocenter 174 of mechanical positioning system 170.

At block 552, processing logic acquires, using the one or more cameras of camera system 110, a second set of images of a radiation beam 160 incident on the phantom 120. The second set of images is of radiation beam 160 incident on the entrance surface of the phantom 120.

At block 554, processing logic determines a center, triangulated in 3D, of the radiation beam 160 incident on the phantom 120 (e.g., pattern centroid 356) based on the second set of images.

At block 556, processing logic determines a beam pointing offset based on the center triangulated in 3D and a location of a source of the radiation beam 160 (e.g., radiation source 304, node of LINAC, spatial location in a room).

At block 558, processing logic calibrates a position of the LINAC 150 based on the beam pointing offset and the relationship (from block 548). In one implementation, a beam vector is determined based on center triangulated in 3D and the location of the radiation source 304. The beam pointing offset magnitude and direction are determined from the beam vector.

Blocks 550-558 may be repeated (e.g., after block 558, the method 540 may restart at 550) if a set of a radiation beams is to be calibrated.

In one implementation, the one or more cameras of camera system 110 are in-line with the beam axis of the radiation beam 160. In another implementation, the one or more cameras are not in-line with a beam axis of the radiation beam and the method further includes calculating pose of the one or more cameras of camera system 110 with respect to the radiation beam axis (e.g., blocks 540-548, not shown in FIG. 5C). At block 542, processing logic acquires, using the plurality of cameras, a third set of images of a pattern 200 overlaid on the X-ray luminescent material while the phantom 120 is not being irradiated to determine pose and focal length of the plurality of cameras of camera system 110. The plurality of cameras of camera system 110 is an array of cameras fixed within a room (e.g., a treatment room). A threshold number of cameras of camera system 110 are needed such that the phantom 120 and radiation pattern 352 at the entrance surface of the phantom 120 are visible on multiple cameras of camera system 110 with each direction of the radiation beam 160. The third set of images may be at a plurality of SAD between the pattern 200 and the LINAC 150.

At block 544, processing logic maps the third set of images to stationary spatial camera positions of the plurality of cameras of camera system 110 to perform a three-dimensional (3D) calibration. The 3D calibration is based on multiple optical checkerboard positions and orientations (e.g., images from a plurality of cameras of camera system 110 at a plurality of SAD). Each camera of camera system 110 of the plurality of cameras of camera system 110 is mapped to a corresponding spatial position.

At block 546, processing logic acquires, using the plurality of cameras of camera system 110, a fourth set of images of the radiation beam 160 incident on the pattern 200 at a plurality of SAD to determine a location of a beam axis 306 with respect to the pattern 200.

At block 548, processing logic determines, based on the pose, the focal length, and the location of the beam axis 306, a relationship between a first centroid 354 of the phantom 120 and a second centroid 356 of the radiation beam 160 incident on the pattern 200. In one implementation, blocks 542-548 may be a one-off procedure if the cameras remain static between tests.

In one implementation, blocks 540-548 may be a camera calibration setup that is a one-off procedure (if pose is repeatable). In another implementation, blocks 540-548 may be required before each calibration procedure (e.g., blocks 550-558) or verification procedure (e.g., method 600) is performed. In one implementation, blocks 502-506 may be generalized to multiple camera configurations and the accuracy of the calibration may improve with multiple cameras 110.

FIG. 5D illustrates a flow diagram of a method 560 for calibration of a position of a LINAC 150 using camera system 110 located at static locations to acquire images of an entrance surface and an exit surface of the phantom 120, in accordance with implementations of the present disclosure.

At block 562, processing logic acquires, using a plurality of cameras of camera system 110, a first set of images of a phantom 120 while the phantom 120 is not being irradiated. In one implementation, the phantom 120 of method 560 may be substrate that is opaque. In one implementation, one or more of the plurality of cameras of camera system 110 acquires an image of the unirradiated entrance surface. The image of the unirradiated entrance surface may further display the light signal at the exit surface. In another implementation, the plurality of cameras of camera system 110 acquires an image of the unirradiated entrance surface and an image of the unirradiated exit surface.

At block 564, processing logic acquires, using the one or more cameras of camera system 110, a second set of images of a radiation beam 160 incident on the phantom 120. Two or more of the second set of images may be used to generate a super-position of the radiation beam 160 incident on an entrance surface (e.g., entrance feature 360) and an exit surface (e.g., exit feature 370) of the phantom 120.

At block 566, processing logic determines a projected isocenter of the radiation source (e.g., LINAC 150) based on the first set of images, geometry of the phantom 120, and position of the phantom 120.

At block 568, processing logic determines a first center, triangulated in 3D, of the radiation beam 160 incident on the entrance surface (e.g., entrance feature 360) and a second center, triangulated in 3D, of the radiation beam incident on the exit surface (e.g., exit feature 370) based on the second set of images.

At block 570, processing logic determines a beam pointing offset based on the first center triangulated in 3D, the second center triangulated in 3D, and the projected isocenter. In one implementation, a beam vector is determined from the first center and the first center without the location of the radiation source 304. The beam vector and projected isocenter are used to determine the beam pointing offset.

At block 572, processing logic calibrates a position of the LINAC 150 based on the beam pointing offset. In some implementations, the beam pointing error from block 630 of FIG. 6 may be applied as a beam pointing offset to mechanical beam positioning devices (e.g., devices of mechanical positioning system 170) to adjust the position of the LINAC 150. The calibration method of any one of methods 400, 500, 520, 540, or 560 and the verification method of method 600 may be iterated. A list of beam pointing offsets that can be applied by the mechanical positioning systems during treatment (e.g., used to amend or replace the existing pointing calibration) may be output (e.g., as a report).

Blocks 562-572 may be repeated (e.g., after block 572, the method 560 may restart at 562) if a set of a radiation beams is to be calibrated.

It should be noted that the above described operations are just one method of calibrating a position of a LINAC 150 and that, in alternative implementations, certain ones of the operations of FIG. 4-5D may be optional or take a simpler form.

FIG. 6 illustrates a flow diagram of a method 600 for verification of a position of a LINAC 150, in accordance with implementations of the present disclosure. In some implementations, method 600 may occur after any one of methods 400, 500, 520, 540, or 560. In some implementations, method 600 may occur without any of methods 400, 500, 520, 540, or 560. Method 600 may occur after a different method for calibration (e.g., a slower method of calibration, a calibration technique using a point detector and a raster scan). Method 600 may be iterated.

At block 610, processing logic acquires, using a camera of camera system 110 of the one or more cameras of camera system 110, a third image of the radiation beam 160 incident on the phantom 120 subsequent to the calibrating of the position of the LINAC 150. The calibrating of the position of the LINAC 150 may include updating the offsets used by the mechanical positioning system 170 in positioning the LINAC 150 for emitting of a radiation beam 160.

At block 620, processing logic calculates a beam pointing error based on the third image and a corresponding image of the second set of images. The second set of images may be of the radiation beam 160 incident on the phantom 120 acquired in any one of methods 400, 500, 520, 540, or 560.

At block 630, processing logic outputs the beam pointing error. The beam pointing error may be output as a list of verification results describing the resulting beam pointing error at each position after the final calibration (e.g., the final calibration after any iterations of calibration) is applied. If only a verification procedure is performed (e.g., as part of system Quality Assurance), then only a report of the verification results may be generated.

Blocks 610-630 may be repeated (e.g., after block 630, the method 600 may restart at 610) if a set of positions (e.g., positions of the LINAC for emitting radiation beams) is to be verified.

It should be noted that the above described operations are just one method of verifying a position of a LINAC 150 and that, in alternative implementations, certain ones of the operations of FIG. 6 may be optional or take a simpler form.

The methods described in FIGS. 4-6 may be used in systems other than a radiation beam 160 incident on a phantom 120.

Figure 7:
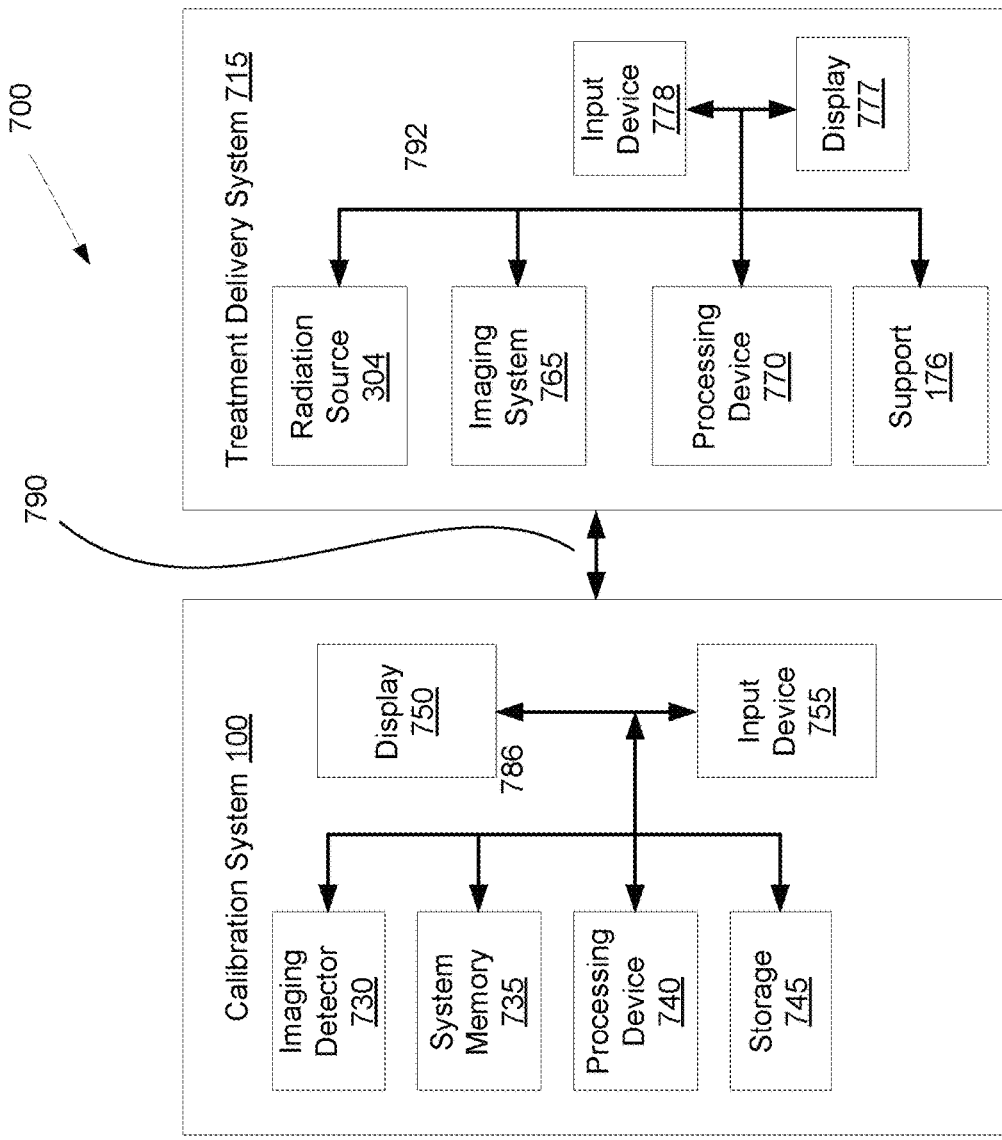
FIG. 7 illustrates systems that may be used in performing calibration of a position of a LINAC, in accordance with implementations of the present disclosure.

FIG. 7 illustrates systems that may be used in performing radiation treatment, in accordance with implementations of the present disclosure. These systems may be used to perform, for example, the methods described above. As described below and illustrated in FIG. 7, a system 700 may include a calibration system 100 and a treatment delivery system 715.

In one implementation, calibration system 100 includes an imaging detector 730 (e.g., one or more cameras of camera system 110) to acquire a first set of images of a phantom 120 without being irradiated and a second set of images of a radiation beam 160 incident on the phantom 120.

In one implementation, imaging detector 730 may be coupled to processing device 740 to control the imaging operation and process image data. In one implementation, calibration system 100 may receive imaging commands from treatment delivery system 715.

Calibration system 100 includes a processing device 740 to calibrate the position of the LINAC 150. Processing device 740 may represent one or more general-purpose processors (e.g., a microprocessor), special purpose processor such as a digital signal processor (DSP) or other type of device such as a controller or field programmable gate array (FPGA). Processing device 740 may be configured to execute instructions for performing beam profile measurement generating operations discussed herein. Processing device 740 may also include other components (not shown) such as memory, storage devices, network adapters and the like. Processing device 740 may be configured to generate digital diagnostic images in a standard format, such as the Digital Imaging and Communications in Medicine (DICOM) format, for example. In other implementations, processing device 740 may generate other standard or non-standard digital image formats. Processing device 740 may transmit diagnostic image files (e.g., the aforementioned DICOM formatted files) to treatment delivery system 715 over a data link 790, which may be, for example, a direct link, a local area network (LAN) link or a wide area network (WAN) link such as the Internet. In addition, the information transferred between systems may either be pulled or pushed across the communication medium connecting the systems, such as in a remote diagnosis or treatment planning configuration. In remote diagnosis or treatment planning, a user may utilize implementations of the present disclosure to diagnose or treat a patient despite the existence of a physical separation between the system user and the patient.

Calibration system 100 may also include system memory 735 that may include a random access memory (RAM), or other dynamic storage devices, coupled to processing device 740 by bus 786, for storing information and instructions to be executed by processing device 740. System memory 735 also may be used for storing temporary variables or other intermediate information during execution of instructions by processing device 740. System memory 735 may also include at least one of a read only memory (ROM) or other static storage device coupled to bus 786 for storing static information and instructions for processing device 740.

Calibration system 100 may also include storage device 745, representing one or more storage devices (e.g., a magnetic disk drive or optical disk drive) coupled to bus 786 for storing information and instructions. Storage device 745 may be used for storing instructions for performing the beam profile measurement steps discussed herein.

Processing device 740 may also be coupled to a display device 750, such as a cathode ray tube (CRT) or liquid crystal display (LCD), for displaying information (e.g., beam profile offset of FIGS. 4-6, beam profile error of FIG. 6, etc.) to the user. An input device 755, such as a keyboard, may be coupled to processing device 740 for communicating at least one of information or command selections to processing device 740. One or more other user input devices (e.g., a mouse, a trackball or cursor direction keys) may also be used to communicate directional information, to select commands for processing device 740 and to control cursor movements on display 750. Processing device 740 may be coupled to system memory 735, storage device 745, display device 750, and input device 755 by a bus 786 or other type of control and communication interface.

In one implementation, the input device 755 may receive input from a user to perform one or more of calibration or verification of a position of a LINAC 150 (e.g., one or more of calibration or verification of the mechanical positioning system 170 coupled to the LINAC 150, etc.). The processing device 740 may transmit a first command to the one or more cameras of camera system 110 to acquire a first set of images of phantom 120 while the phantom is not being irradiated, transmit a second command to emit a radiation beam 160 using the LINAC 150, transmit a third command to the one or more cameras of camera system 110 to acquire a second set of images of a radiation beam 160 incident on the phantom 120, determine a beam pointing offset based on the first set of images and the second set of images, and transmit a fourth command to calibrate a position of the LINAC 150 based on the beam pointing offset. The processing device 740 may generate a list of beam pointing offsets and a list of beam pointing errors to be displayed via display device 750.

Calibration system 100 may share its database (e.g., data stored in storage 745) with a treatment delivery system, such as treatment delivery system 715, so that it may not be necessary to export from the treatment planning system prior to treatment delivery. Calibration system 100 may be linked to treatment delivery system 715 via a data link 790, which in one implementation may be a direct link, a LAN link or a WAN link.

In one implementation, treatment delivery system 715 includes one or more of a therapeutic or surgical radiation source 304 (e.g., LINAC 150) to administer a prescribed radiation dose (e.g., radiation beam 160) to a target volume (e.g., patient, phantom 120, etc.). Treatment delivery system 715 may also include imaging system 765 to perform computed tomography (CT) such as cone beam CT, and images generated by imaging system 765 may be two-dimensional (2D) or three-dimensional (3D).

Treatment delivery system 715 may also include a processing device 770 to control radiation source 304, receive and process data from calibration system 100, and control a support device such as a support 176. Processing device 770 may include one or more general-purpose processors (e.g., a microprocessor), a special purpose processor such as a digital signal processor (DSP) or other type of device such as a controller or field programmable gate array (FPGA). The processing device 770 may be configured to execute instructions to position the LINAC 150 (e.g., via calibration of the mechanical positioning system 170).

Treatment delivery system 715 also includes system memory such as a random access memory (RAM), or other dynamic storage devices, coupled to a processing device, for storing information and instructions to be executed by the processing device. The system memory also may be used for storing temporary variables or other intermediate information during execution of instructions by the processing device 770 (e.g., instructions received from calibration system 100) or processing device 740. The system memory may also include one or more of a read only memory (ROM) or other static storage device for storing static information and instructions for the processing device.

Treatment delivery system 715 also includes a storage device, representing one or more storage devices (e.g., a magnetic disk drive or optical disk drive) for storing information and instructions (e.g., instructions received from calibration system 100). Processing device 770 may be coupled to radiation source 304 and support 176 by a bus 792 or other type of control and communication interface.

Processing device 770 may implement methods to manage timing of diagnostic x-ray imaging in order to maintain alignment of a target with a radiation treatment beam delivered by the radiation source 304. Processing device 770 may implement methods to manage timing of diagnostic x-ray imaging in order to maintain alignment of a target with a set of radiation treatment beams delivered by the radiation source 304.

In one implementation, the treatment delivery system 715 includes an input device 778 and a display 777 connected with processing device 770 via bus 792. The display 777 can show trend data that identifies a rate of target movement (e.g., a rate of movement of a target volume that is under treatment). The display 777 can also show a current radiation exposure of a patient and a projected radiation exposure for the patient. The input device 778 can enable a clinician to adjust parameters of a treatment delivery plan during treatment.

It should be noted that when data links 786 and 790 are implemented as LAN or WAN connections, at least one of calibration system 100 or treatment delivery system 715 may be in decentralized locations such that the systems may be physically remote from each other. Alternatively, at least one of calibration system 100 or treatment delivery system 715 may be integrated with each other in one or more systems.

Figure 8:
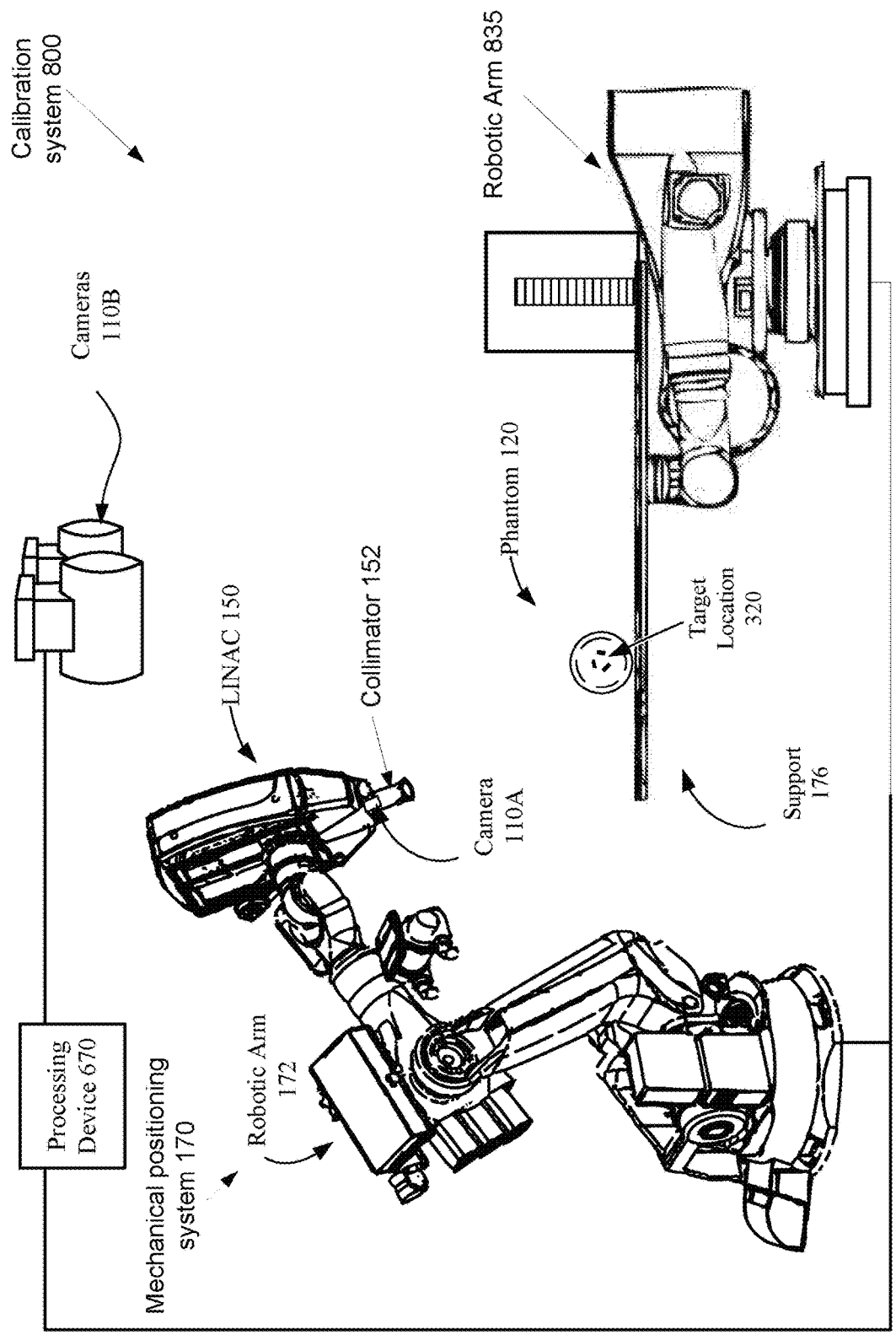
FIG. 8 illustrates configurations of a calibration system, in accordance with implementations of the present disclosure.

FIG. 8 illustrates configurations of calibration system 800, in accordance with implementations of the present disclosure. In one implementation, the calibration system 800 includes camera 110A coupled to a LINAC 150. In another implementation, the calibration system 800 includes cameras 110B that are stationary. LINAC 150 acts as a radiation treatment source. LINAC 150 is coupled to a mechanical positioning system 170 including a robotic arm 172. In one implementation, the LINAC 150 and camera 110A are mounted on the end of a robotic arm 172 having multiple (e.g., 5 or more) degrees of freedom in order to position the LINAC 150 to irradiate a pathological anatomy (e.g., target location 320) with radiation beams 160 delivered from many angles, in many planes, in an operating volume around a phantom 120, and to capture images by the camera 110 of the radiation beam 160 incident on the phantom 120. Treatment may involve beam paths with a single isocenter, multiple isocenters, or with a non-isocentric approach. Alternatively, other types of image guided radiation treatment (IGRT) systems may be used. In one alternative implementation, the LINAC 150 and one or more cameras 110 may be mounted on a gantry based system (e.g., robotic gantry) to provide isocentric beam paths (see FIG. 9). In one particular implementation, the IGRT system is the Vero SBRT System (referred to as TM200 in Japan), a joint product of Mitsubishi Heavy Industries Ltd., of Tokyo Japan and BrainLAB AG of Germany, that utilizes a rigid O-ring based gantry (see FIG. 9).

In one implementation, the LINAC 150 and camera 110 may be positioned at multiple different nodes (predefined positions at which the robot stops and radiation may be delivered) during treatment by moving the robotic arm 172. At the nodes, the LINAC 150 can deliver one or more radiation beams 160 to a target location 320. The nodes may be arranged in an approximately spherical distribution about a phantom 120. The particular number of nodes and the number of radiation beams 160 applied at each node may vary as a function of the location and type of pathological anatomy to be treated. For example, the number of nodes may vary from 50 to 300, or more preferably 15 to 100 nodes and the number of treatment beams 114 may vary from 700 to 3200, or more preferably 50 to 300. In one implementation, there are at least 1000 nodes.

Referring to FIG. 8, calibration system 700, in accordance with one implementation of the present disclosure, includes fixed cameras 110B coupled to a processing device 670. Alternatively, the cameras 110B may be mobile, in which case they may be repositioned to at least one of maintain alignment with the target location 320, image the target location 320 from different orientations, or to acquire many images and reconstruct a three-dimensional (3D) cone-beam CT. In one implementation the cameras 110 are not point cameras, but rather camera arrays, as would be appreciated by the skilled artisan. In one implementation, LINAC 150 serves as an imaging source (whether gantry or robot mounted), where the LINAC power level is reduced to acceptable levels for imaging.

Calibration system 800 may perform computed tomography (CT) such as cone beam CT, and images generated by calibration system 800 may be two-dimensional (2D) or three-dimensional (3D). The cameras 110B may be mounted in fixed positions on the ceiling of an operating room and may be aligned to acquire images from two different angular positions (e.g., separated by 90 degrees) to intersect at a machine isocenter (referred to herein as a treatment center, which provides a reference point for positioning the phantom 120 on a support 176 during emitting of radiation beams 160). In one implementation, calibration system 800 provides stereoscopic imaging of the target location 320 and the surrounding volume of interest (VOI). In other implementations, calibration system 800 may include more than cameras 110B, and any of the cameras 110B may be movable rather than fixed. Phantom 120 may be fabricated from or coated with a scintillating material that converts the radiation beam 160 to visible light (e.g., amorphous silicon), and the light may be converted to a digital image that can be compared with a reference image during an image registration process that transforms a coordinate system of the digital image to a coordinate system of the reference image, as is well known to the skilled artisan. The reference image may be, for example, a digitally reconstructed radiograph (DRR), which is a virtual x-ray image that is generated from a 3D CT image based on simulating the x-ray image formation process by casting rays through the CT image.

Figure 9:
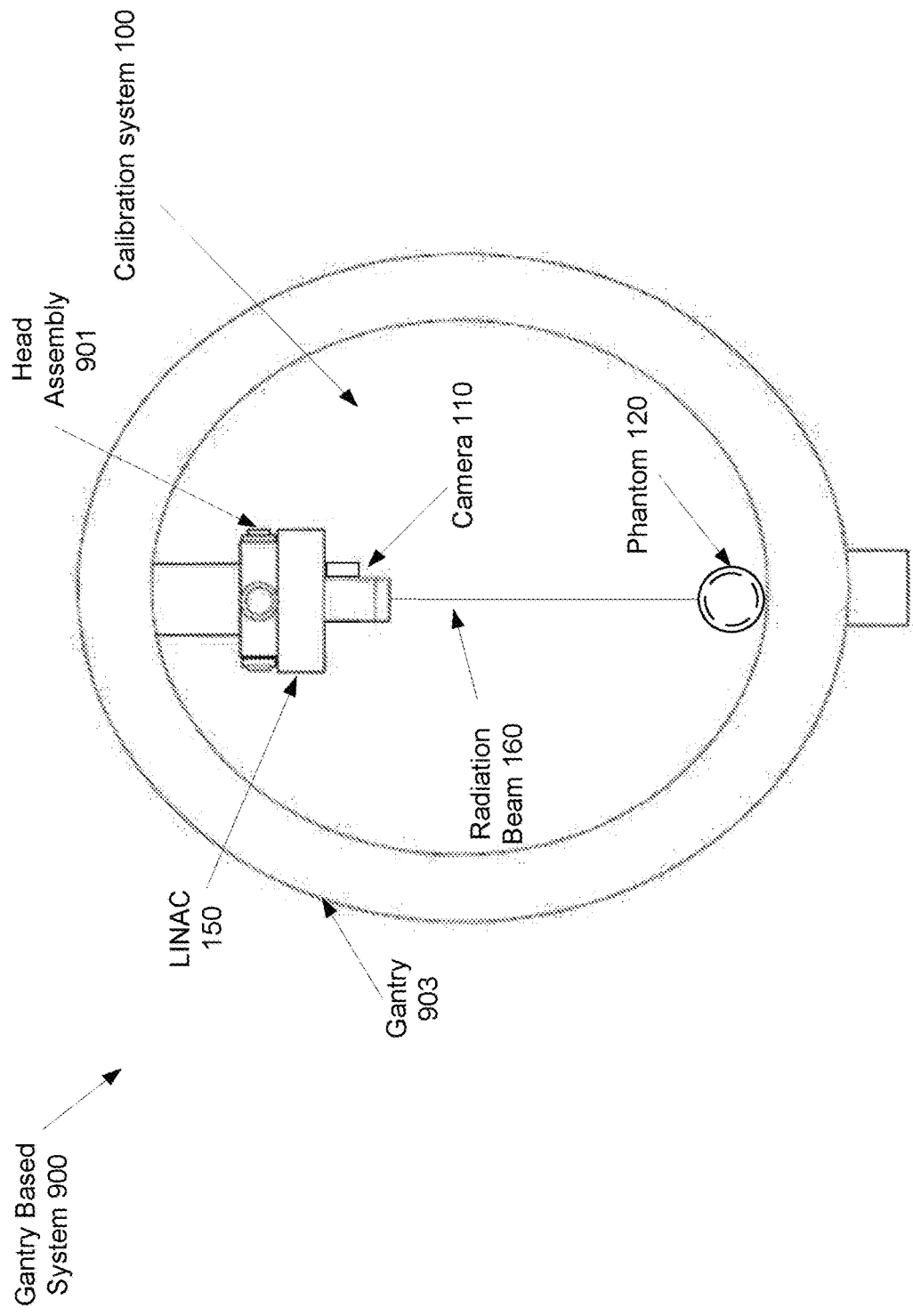
FIG. 9 illustrates a gantry based intensity modulated radiotherapy system, in accordance with implementations of the present disclosure.

FIG. 9 illustrates a gantry based intensity modulated radiotherapy (IMRT) system 900, in accordance with implementations of the present disclosure. In one implementation, the LINAC 150 is mounted on a gantry 903 (e.g., a mechanical positioning system 170). In a gantry based system 900, a radiation source (e.g., a LINAC 150) having a head assembly 901 is mounted on a gantry 903 in such a way that they rotate in a plane corresponding to an axial slice of the phantom 120. Radiation beams 160 are then delivered from several positions on the circular plane of rotation (e.g., around an axis of rotation). In one implementation, one or more cameras 110 may be coupled to the LINAC 150. In another implementation, cameras are statically located. In IMRT, the camera 110 may acquire a first set of images of the phantom 120 without being irradiated and a second set of images of a radiation beam 160 incident on the phantom 120. The images may be acquired at different positions of the LINAC 150. The resulting system generates arbitrarily shaped radiation beams 160 that intersect each other at the isocenter to deliver a dose distribution to the target location. In one implementation, the gantry based system 900 may be a c-arm based system.

Figure 10:
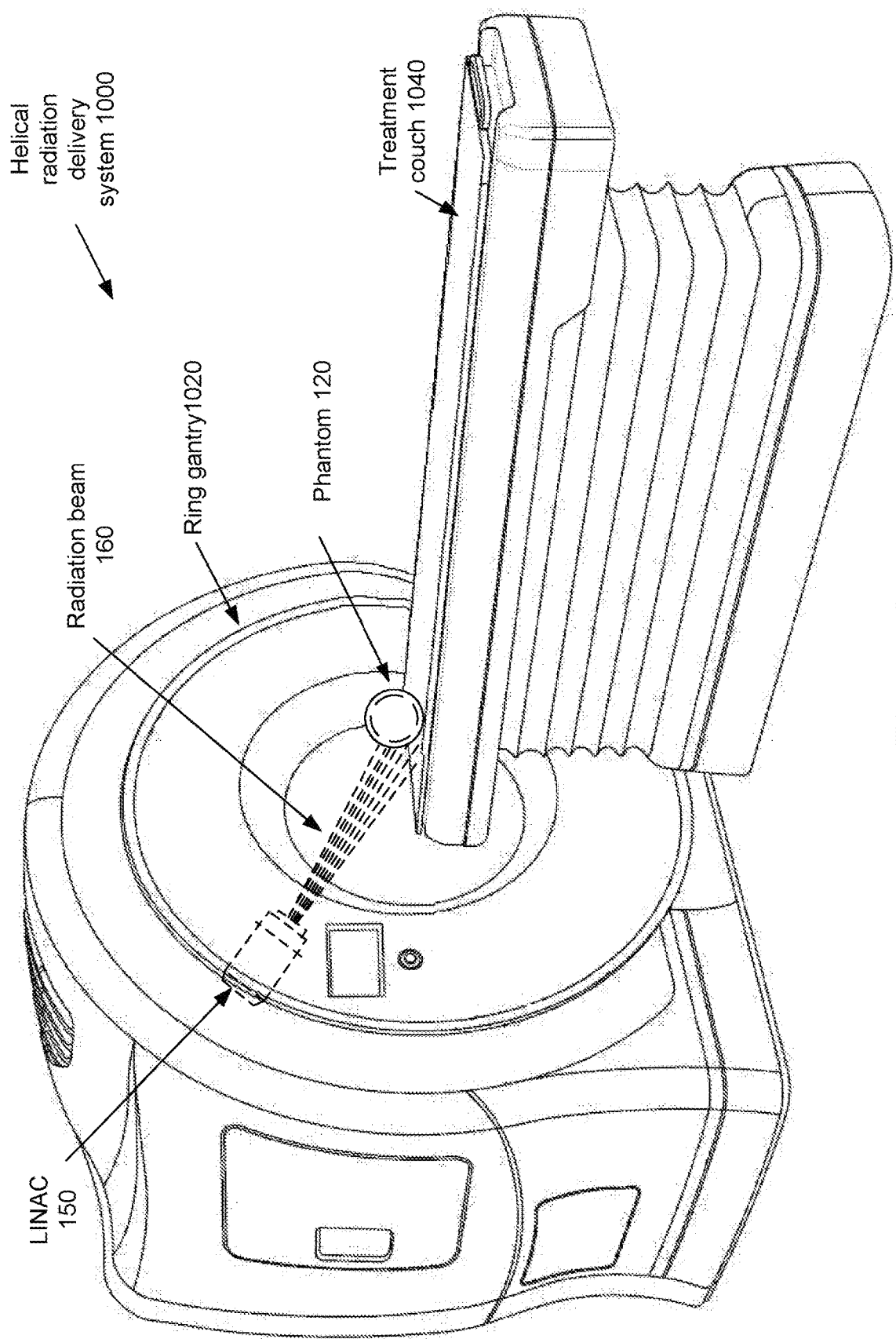
FIG. 10 illustrates a helical radiation delivery system, in accordance with implementations of the present disclosure.

FIG. 10 illustrates a helical radiation delivery system 1000, in accordance with implementations of the present disclosure. The helical radiation delivery radiotherapy system 1000 includes a LINAC 150 mounted to a ring gantry 1020. The ring gantry 1020 has a toroidal shape and the target location 320 (e.g., phantom 120, a patient, etc.) is moved through a bore of the toroidal shape of the ring gantry 1020. A central axis passes through the center of the bore. In one implementation, a radiation beam 160 is generated by a LINAC 150 that is mounted to a ring gantry 1020 that rotates around the central axis to deliver the radiation beam 160 to a phantom 120 from various angles. While the radiation beams 160 are being delivered, the phantom 120 is on a treatment couch 1040 (e.g., an adjustable table, support 176) and the phantom 120 is simultaneously moved through the bore of the ring gantry 1020 allowing horizontal movement of the radiation beam 160 in relation to the phantom 120 without horizontally moving the LINAC 150 or the phantom 120. The treatment couch 1040 may move the phantom in a vertical direction so that images may be acquired at different SAD 330.

In some implementations, the LINAC 150 may be mounted to a C-arm gantry in a cantilever-like manner, which rotates the LINAC 150 about the axis passing through the isocenter of the ring gantry 1020. In other implementations, the LINAC 150 may be mounted to a robotic arm having multiple (e.g., 5 or more) degrees of freedom in order to position the LINAC 150 around the ring gantry 1020 to irradiate the phantom 120 that is moved (e.g., horizontally, vertically) by the treatment couch 1040.

It will be apparent from the foregoing description that aspects of the present disclosure may be embodied, at least in part, in software. That is, the techniques may be carried out in a computer system or other data processing system in response to a processing device 770, for example, executing sequences of instructions contained in a memory. In various implementations, hardware circuitry may be used in combination with software instructions to implement the present disclosure. Thus, the techniques are not limited to any specific combination of hardware circuitry and software or to any particular source for the instructions executed by the data processing system. In addition, throughout this description, various functions and operations may be described as being performed by or caused by software code to simplify description. However, those skilled in the art will recognize what is meant by such expressions is that the functions result from execution of the code by processing device 770.

A machine-readable medium can be used to store software and data which when executed by a general purpose or special purpose data processing system causes the system to perform various methods of the present disclosure. This executable software and data may be stored in various places including, for example, system memory and storage or any other device that is capable of storing software programs and/or data. Thus, a machine-readable medium includes any mechanism that provides (i.e., stores) information in a form accessible by a machine (e.g., a computer, network device, personal digital assistant, manufacturing tool, any device with a set of one or more processors, etc.). For example, a machine-readable medium includes recordable/non-recordable media such as read only memory (ROM), random access memory (RAM), magnetic disk storage media, optical storage media, flash memory devices, etc. The machine-readable medium may be a non-transitory computer readable storage medium.

Unless stated otherwise as apparent from the foregoing discussion, it will be appreciated that terms such as "acquiring," "determining," "calibrating," "mapping," "outputting," "applying," or the like may refer to the actions and processes of a computer system, or similar electronic computing device, that manipulates and transforms data represented as physical (e.g., electronic) quantities within the computer system's registers and memories into other data similarly represented as physical within the computer system memories or registers or other such information storage or display devices. Implementations of the methods described herein may be implemented using computer software. If written in a programming language conforming to a recognized standard, sequences of instructions designed to implement the methods can be compiled for execution on a variety of hardware platforms and for interface to a variety of operating systems. In addition, implementations of the present disclosure are not described with reference to any particular programming language. It will be appreciated that a variety of programming languages may be used to implement implementations of the present disclosure.

It should be noted that the methods and apparatus described herein are not limited to use only with medical diagnostic imaging and treatment. In alternative implementations, the methods and apparatus herein may be used in applications outside of the medical technology field, such as industrial imaging and non-destructive testing of materials. In such applications, for example, "treatment" may refer generally to the effectuation of an operation controlled by the treatment planning system, such as the application of a beam (e.g., radiation, acoustic, etc.) and "target" may refer to a non-anatomical object or area.

In the foregoing specification, the disclosure has been described with reference to specific exemplary implementations thereof. It will, however, be evident that various modifications and changes may be made thereto without departing from the broader spirit and scope of the disclosure as set forth in the appended claims. The specification and drawings are, accordingly, to be regarded in an illustrative sense rather than a restrictive sense.

What is claimed is:

1. A method of calibration in a radiation delivery system, comprising:
    acquiring, using a camera, an image of a radiation beam incident on a phantom, the radiation beam being emitted by a radiation source of the radiation delivery system, the phantom comprising an X-ray luminescent material,
    determining a beam pointing offset based on the image;
    identifying, using the camera, a pattern overlaid on the X-ray luminescent material;
    determining, based on the pattern overlaid on the X-ray luminescent material, a relative position of the camera with respect to a beam axis of the radiation beam;
    determining, based on the relative position of the camera with respect to the beam axis, a relationship between a centroid of the phantom and a different centroid of the radiation beam incident on the pattern; and
    calibrating a position of the radiation source of the radiation delivery system based on the beam pointing offset and the relationship between the centroid of the phantom and the different centroid of the radiation beam incident on the pattern.

2. The method of claim 1, further comprising:
    acquiring, using the camera, a second image of the radiation beam incident on the phantom subsequent to the calibrating of the position of the radiation source;
    calculating a beam pointing error based on the second image and the image; and
    outputting the beam pointing error.

3. A calibration system comprising:
    a phantom comprising an X-ray luminescent material;
    a camera system of the calibration system to:
        acquire an image of a radiation beam incident on the phantom, the radiation beam being emitted by a radiation source;
        identify a pattern overlaid on the X-ray luminescent material; and
    a processing device, operatively coupled with the camera, to:
        determine a beam pointing offset based on the image;
        determine, based on the pattern overlaid on the X-ray luminescent material, a relative position of the camera system with respect to a beam axis of the radiation beam;
        determine, based on the relative position of the camera system with respect to the beam axis, a relationship between a centroid of the phantom and a different centroid of the radiation beam incident on the pattern; and
        calibrate a position of the radiation source based on the beam pointing offset and the relationship between the centroid of the phantom and the different centroid of the radiation beam incident on the pattern.

4. The calibration system of claim 3, wherein the camera system comprises one or more cameras, wherein the one or more cameras to:
    acquire a first set of images of the phantom while the phantom is not being irradiated;
    acquire a second set of images of the radiation beam incident on the phantom, the second set of images comprising the image, wherein determining the beam pointing offset is further based on the first set of images and the second set of images.

5. The calibration system of claim 4, wherein:
    each of the second set of images is of the radiation beam incident on an entrance surface of the phantom;
    each of the one or more cameras is coupled to a head of the radiation source; and
    the processing device is further to:
        determine a projected isocenter of the radiation source based on the first set of images, geometry of the phantom, and position of the phantom;
        determine a third centroid of the radiation beam incident on the phantom is based on the second set of images, wherein the beam pointing offset is based on comparing the projected isocenter and the third centroid.

6. The calibration system of claim 4, wherein:
    each of the second set of images is a super-position of the radiation beam incident on an entrance surface and an exit surface of the phantom;
    the one or more cameras are coupled to a head of the radiation source; and
    the processing device is further to:
        determine a projected isocenter of the radiation source based on the first set of images, geometry of the phantom, and position of the phantom; and
        determine a half-way point between a first centroid of the radiation beam incident on the entrance surface and a second centroid of the radiation beam incident on the exit surface is based on the second set of images, wherein the beam pointing offset is based on a distance between the projected isocenter and the half-way point.

7. The calibration system of claim 4, wherein:
    the second set of images is of the radiation beam incident on an entrance surface of the phantom;
    the one or more cameras is a plurality of cameras that are positioned at static locations;
    the processing device is further to:
        determine a center, triangulated in 3D, of the radiation beam incident on the phantom based on the second set of images, wherein the beam pointing offset is based on the center triangulated in 3D and a location of a source of the radiation beam.

8. The calibration system of claim 4, wherein:
    the second set of images are used to generate super-position of the radiation beam incident on an entrance surface and an exit surface of the phantom;
    the one or more cameras is a plurality of cameras that are positioned at static locations;

the processing device is further to:
   determine a projected isocenter of the radiation source is based on the first set of images, geometry of the phantom, and position of the phantom; and
   determine a first center, triangulated in 3D, of the radiation beam incident on the entrance surface and a second center, triangulated in 3D, of the radiation beam incident on the exit surface are based on the second set of images, wherein the beam pointing offset is based on the first center triangulated in 3D, the second center triangulated in 3D, and the projected isocenter.

9. The calibration system of claim 4, wherein:
the one or more cameras have sensor distortion and lens distortion; and
the processing device is to apply corrections for at least one of the sensor distortion or the lens distortion to the first set of images and the second set of images.

10. The calibration system of claim 3, wherein:
the camera is to acquire a second image of the radiation beam incident on the phantom subsequent to the calibrating of the position of the radiation source;
the processing device is further to:
   calculate a beam pointing error based on the third image and the image; and
   output the beam pointing error.

\* \* \* \* \*